US007943361B2

(12) United States Patent
Tyagi et al.

(10) Patent No.: US 7,943,361 B2
(45) Date of Patent: May 17, 2011

(54) **MUTANTS OF *MYCOBACTERIA* AND PROCESS THEREOF**

(75) Inventors: Anil Kumar Tyagi, New Delhi (IN); Ramandeep Singh, New Delhi (IN); Vivek Rao, New Delhi (IN); Vadakkuppattu Devasenapathi Ramanathan, Chennai (IN); Chinnambedy Nainarappan Paramasivan, Chennai (IN); Paranji Ramaiyenger Narayanan, Chennai (IN); Yogendra Singh, Delhi (IN)

(73) Assignees: Indian Council of Medical Research, New Delhi (IN); University of Delhi, New Delhi (IN)

( * ) Notice: Subject to any disclaimer, the term of this patent is extended or adjusted under 35 U.S.C. 154(b) by 1455 days.

(21) Appl. No.: 10/560,605

(22) PCT Filed: Jul. 9, 2004

(86) PCT No.: PCT/IN2004/000203
§ 371 (c)(1),
(2), (4) Date: Mar. 23, 2006

(87) PCT Pub. No.: WO2005/005639
PCT Pub. Date: Jan. 20, 2005

(65) Prior Publication Data
US 2009/0215031 A1    Aug. 27, 2009

(30) Foreign Application Priority Data
Jul. 9, 2003  (IN) .............................. 882/DEL/2003

(51) Int. Cl.
*C12N 1/21*     (2006.01)
*C07H 21/04*   (2006.01)

(52) U.S. Cl. ................. 435/252.3; 435/253.1; 536/23.1; 536/23.7; 536/24.32; 536/24.33

(58) Field of Classification Search ........................ None
See application file for complete search history.

(56) References Cited

FOREIGN PATENT DOCUMENTS
WO    WO 01/81422    11/2001
WO    WO 0181422 A1 *  11/2001

OTHER PUBLICATIONS

Koul, A. et al. Journal of Bacteriology 182(19):5425-5432 (Oct. 2000).*
Cowley, S.C. et al. Research in Microbiology 153:233-241 (Mar. 2002).*
Singh et al. "Disruption of *mptpB* impairs the ability of *Mycobacterium tuberculosis* to survive in guinea pigs." *Molecular Microbiology* vol. 50. No. 3. 2003. pp. 751-762.
Database Embl. Jun. 19, 2003—Wang et al. Identification of essential genes in microorganism. XP002317369.
Koul et al. "Cloning and Characterization of Secretory Tyrosine Phosphatases of *Mycobacterium tuberculosis.*" *J. of Bacteriology.* vol. 182. No. 19. 2000. pp. 5425-5432.

* cited by examiner

*Primary Examiner* — Diana B Johannsen
(74) *Attorney, Agent, or Firm* — Merchant & Gould P.C.

(57) ABSTRACT

The present invention provides mutant *Mycobacterium* strains harboring a modified tyrosine phosphatase gene (mptpA or mptpB) wherein the mutant *Mycobacterium* strain is incapable of expressing the active tyrosine phosphatase. The invention provides a method for developing the said mutant strain from either *Mycobacterium tuberculosis* or *Mycobacterium bovis*. The mptpA or mptpB gene may be modified by replacing the internal sequences with an antibiotic resistance marker gene, which disrupts the expression of the active gene. The invention further provides a recombinant vector comprising the modified mptpA or mptpB which may be used to develop the mutant strains of mycobacteria. The invention provides a method to assess the role of tyrosine phosphatases MptpA and MptpB in the virulence and pathogenesis of *Mycobacterium* which can be used as potential targets for developing anti-tubercular drug.

7 Claims, 12 Drawing Sheets

MUTANTS OF *MYCOBACTERIA* AND PROCESS THEREOF

FIELD OF THE INVENTION

Figure 1:
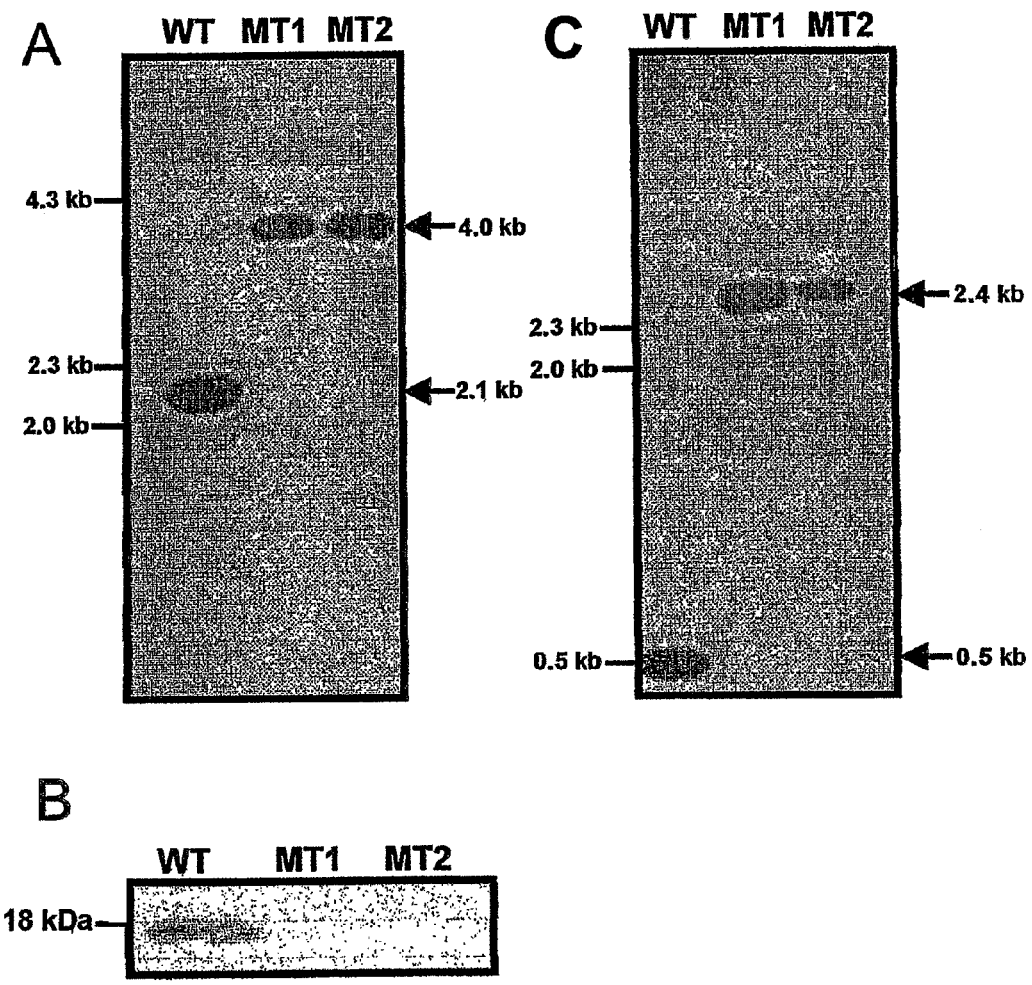

The present invention provides an attenuated mutant *Mycobacterium* strain wherein the mutant strain is incapable of expressing the active tyrosine phosphatase and is impaired in its ability to survive in activated macrophages and animals. The invention also provides a method for developing a mutant *Mycobacterium* strain with modified tyrosine phosphatase gene in its genome. The invention also provides a method to assess the role of tyrosine phosphatase in virulence and pathogenesis of mycobacteria and identifies these as potential targets for developing new anti-tubercular drugs.

BACKGROUND OF THE INVENTION

One-third of world's population is infected with *M. tuberculosis* asymptomatically. Eight million new cases of active diseases develop each year & three million people succumb to this disease every year (Dye et al., 1999). With the advent of HIV & emergence of multidrug resistant strains of *M. tuberculosis*, the problem has increased manifold (Horsburgh, 1991; Barnes et al., 1991 and Bloch et al., 1994). The current treatment of disease usually involves combination chemotherapy based on isoniazid, pyrazinamide, rifampicin & ethambutol. In general, 6 months long course is required for effective treatment, which often results in poor compliance on the part of patients, who stop drug intake as soon as they begin to feel better. This leads to development of drug resistant forms of bacilli, which are able to survive routine drug therapy. Multidrug resistant tuberculosis (MDR-TB) is defined as a disease due to tubercle bacilli resistant to at least isoniazid and rifampicin, the two most powerful anti-tubercular drugs. Such a precarious scenario demands development of new drugs that can act on new targets and can be effective in relatively shorter periods so that the patients do not develop resistance to these drugs. The present invention can lead to the development of such target specific anti-tubercular drugs useful for short-term therapies.

Sequence analysis of various prokaryotes has shown the presence of eukaryotic like serine/threonine and tyrosine phosphatases in bacterial pathogens. In various pathogenic bacteria like *Yersinia pseudotuberculosis, Salmonella typhimurium* and enteropathogenic *E. coli* tyrosine phosphatses have been shown to act as major virulence determinants (Guan and Dixon., 1990; Galyov et al., 1993 and Kaniga et al., 1996)

YopH, one of the PTPases, is encoded by the yersiniae virulence plasmid and has been identified as an essential virulence factor (Bliska et al., 1991). YopH comprises of several domains including amino terminal sequences involved in secretion, translocation and chaperone binding; a central proline rich SH3—binding domain and a carboxyl terminal catalytic domain that is homologous to a domain in the eukaryotic PTPases (Sory et al., 1995). It is postulated that YopH disrupts a general phagocytic mechanism as both Fc receptor and complement mediated phagocytosis is inhibited by YopH. (Ruckdeschel et al., 1996 and Fallman et al., 1995). Two of the YopH substrates, p130$^{cas}$ and paxillin are proteins involved in connecting integrins to the actin cytoskeleton and the third one is a tyrosine kinase (Persson et al., 1997 and Black et al., 1997). The possible explanation for the role of YopH protein is that it inhibits uptake of bacteria mediated by the interaction of the bacterial outer membrane protein invasin with cellular β1 integrin. According to this model, invasin binding stimulates tyrosine phosphorylation of cellular targets, leading to cytoskeletal rearrangements and bacterial uptake. YopH dephosphorylates the protein required for this activity. Recent studies have shown that YopH also inhibits Akt pathway and phosphatidylinositol 3-kinase dependent secretion of interleukin 2 in macrophages (Sauvonnet et al., 2002).

*S. typhimurium* encodes a tyrosine phosphatase, SptP comprised of modular domains. The amino-terminus of SptP exhibits sequence homology to the Exotoxin S from *P. aeruginosa* and YopE from *Yersinia* spp. Exotoxin S is an ADP ribosyl transferase that has been implicated in *P. aeruginosa* in the induction of host cell injury and is known to be a virulence factor of *P. aeruginosa*. The carboxyl terminus of SptP showed homology to the eukaryotic like protein tyrosine phosphatases. The carboxyl terminus of SptP protein is homologous to YopH and the catalytic domain of the eukaryotic PTPase. The cysteine residue at position 481 is essential for its catalytic activity as mutation of this conserved cysteine residue abolishes the phosphatase activity (Kaniga et al., 1996). Kaniga et al showed that sptP mutants are defective in the colonization of spleens of orally infected BALB/c mice. SptP has been shown to possess an in vitro GTPase activating protein (GAP) activity towards two host GTP binding proteins, Rac-1 and Cdc42 that play an important role in the cytoskeletal dynamics (Fu and Galan, 1999). It has been suggested that the GAP activity of SptP could down regulate signaling through Cdc42 and Rac that could rebuild the actin cytoskeleton after *Salmonella* entry. Fu and Galan have shown that microinjection of purified GST-SptP into cultured cells results in the disruption of actin cytoskeleton and the disappearance of stress fibers (Fu and Galan, 1999).

PRIOR ART

Allelic exchange by homologous recombination is a powerful toot to study gene functions, identification of virulence factors and development of auxotrophic mutants. "Gene knockout" technique involves the replacement of a wild type gene with it's non-functional counterpart. Such targeted mutations are widely used to study gene functions in mammalian, eukaryotic and bacterial cells (Guilhot et al., 1992; Myers et al., 1994; Reyrat et al., 1995; Baulard et al., 1996; Balsubramaninan et al., 1996; Azad et al., 1996; Azad et al., 1997; Hinds et al., 1999; parish et al., 1999; Pelicic et al., 1997; Bardarov et al., 1997 and Raynaud et al., 2002).

Sequence analysis of *M. tuberculosis* genome revealed the presence of 11 serine/threonine kinases and two tyrosine phosphatases (Cole et al., 1998). Both genes having sequence homology with known tyrosine phosphatases were PCR amplified by using gene specific primers and *M. tuberculosis* genomic DNA, cloned in a prokaryotic expression vector, pGEX5x-3 and purified from *E. coli* as GST fusion proteins (Koul et al., 2000). The GST fusion proteins were able to dephosphorylate the phospho-tyrosine residue of myelin basic protein but were unable to dephosphorylate phosphoserine and phospho-threonine residues of myelin basic protein. Site directed mutagenesis of cysteine residues in the catalytic motif (Cys11 in the case of MptpA and Cys160 in the case of MptpB) abolished the enzymatic activity (Koul et al., 2000). By Southern blot analysis, it was revealed that mptpA is present in fast growing as well as slow growing species of mycobacteria. However, while the mptpB was present in slow growers it was found to be absent in *M. smegmatis*, a fast growing species. (Koul et al., 2000). The present invention was undertaken since the role of tyrosine phosphatase in the virulence and pathogenesis of *mycobacterium* was not known.

OBJECTS OF THE INVENTION

The main objective of the present invention is to develop a *mycobacterium* strain with a modified tyrosine phosphatase gene in its genome, wherein the mutant *Mycobacterium* strain is incapable of expressing the active tyrosine phosphatase. The *Mycobacterium* species is selected from a group consisting of *M. tuberculosis* and *M. bovis*.

Another object of the present invention is to provide a method for assessing the role of tyrosine phosphatase in the virulence and pathogenesis of *Mycobacterium* in particular *M. tuberculosis*.

Another object of the present invention is to develop a mutant strain of *M. tuberculosis*, which is devoid of the tyrosine phosphatase activity associated with MptpA.

Another object of the present invention is to develop a mutant strain of *M. tuberculosis*, which is devoid of the tyrosine phosphatase activity associated with MptpB.

Still another object of the present invention is to construct a recombinant vector, wherein the recombinant vector carries the mptpA gene along with its flanking regions and the internal region of mptpA has been substituted by gene conferring resistance to hygromycin.

Still another object of the invention is to insert a second antibiotic resistance marker in the vector backbone particularly kanamycin resistance marker to obtain recombinant vector, pAKΔA.

Another object of the present invention is to construct a recombinant vector, wherein the recombinant vector carries the mptpB gene along with its flanking regions and the internal region of mptpB has been substituted by gene conferring resistance to hygromycin.

Still another object of the invention is to insert a second antibiotic resistance marker in the vector backbone particularly kanamycin resistance marker to obtain recombinant vector, pBKΔB.

Another object of the invention is to modify the mptpA in the genome of *Mycobacterium* strain by homologous recombination using alkali denatured vector, pAKΔA.

Another object of the present invention is to confirm by Southern blot and immuno blot analysis that gene encoding mptpA is modified in the genome of mptpA mutant *Mycobacterium* strain.

Another object of the present invention is to assess the role of MptpA in the survival of *mycobacterium* in activated macrophages.

Another object of the present invention is to assess the role of MptpA in the survival of mycobacteria in animals, where MptpA can be a potential target for developing new anti-tubercular drugs.

Another object of the invention is to modify mptpB in the genome of *Mycobacterium* by homologous recombination using U.V. irradiated vector, pBKΔB.

Another object of the present invention is to confirm by Southern blot and immuno blot analysis that gene encoding mptpB is modified in the genome of mptpB mutant strain.

Another object of the present Invention is to assess the role of MptpB in the survival of *mycobacterium* in activated macrophages.

Another object of the present invention is to assess the role of MptpB in the survival of mycobacteria in animals, where MptpB can be a potential target for developing new anti-tubercular drugs.

SUMMARY OF THE INVENTION

The present invention relates to an attenuated mutant *Mycobacterium* strain having modified tyrosine phosphatase gene wherein the said mutant is incapable of expressing the active tyrosine phosphatase. The invention provides in particular mutant strains of *Mycobacterium tuberculosis* and *Mycobacterium bovis*.

The present invention relates to two tyrosine phosphatase genes mptpA and mptpB and the role of protein tyrosine phosphatases in the virulence and pathogenesis of *Mycobacterium*.

The present invention also relates to two mycobacterial tyrosine phosphatases (MptpA and MptpB) as potential targets for developing new anti-tubercular drugs.

Further, the invention provides a method for developing an attenuated mutant strain of *Mycobacterium* wherein the tyrosine phosphatase gene is modified in its genome and the said mutant strain is incapable of expressing the active product of tyrosine phophatase gene Further, the present invention providesa recombinant vector comprising the modified tyrosine phosphatase gene (mptpA or mptpB).

Further, the recombinant vector contains a selectable marker present within the mptpA or mptpB gene that may be useful for selection of primary recombinant mycobacteria.

Further, a second antibiotic resistance marker is inserted in the vector backbone to obtain the recombinant vector pAKΔA or pBKΔB.

Further, the recombinant vector may be used to develop mutant strain of *Mycobacterium* wherein homologous recombination may be used to replace active tyrosine phosphatase gene from the wild type strain of *Mycobacterium* by a double cross-over event with a modified tyrosine phosphatase gene.

Further, the mutant strain of *Mycobacterium* may be selected based on the presence of antibiotic resistance marker within the modified tyrosine phosphatase gene.

Further, the invention can be used to develop mutant strains of *Mycobacterium* particularly *Mycobacterium tuberculosis* and *Mycobacterium bovis*.

Further, the invention provides a method for assessing of the role of tyrosine phosphatase in the virulence and pathogenesis of *Mycobacterium*, particularly *Mycobacterium tuberculosis*. Further, the mutant strain of *Mycobacterium* having modified tyrosine phosphatase show reduced survival in the activated macrophages and animals.

BRIEF DESCRIPTION OF THE ACCOMPANYING DRAWINGS

FIG. 1:
(A) Southern Blot analysis of the wild type (WT) and mptpA mutant (MT1 and MT2) strains of *M. tuberculosis*.
Genomic DNAs (3 µg) from the wild type (WT) and mptpA mutant strain (MT1 and MT2) of *M. tuberculosis* were digested with Not I, separated on 1.2% agarose gel, transferred to Hybond N membrane and probed with $^{32}$P labeled mptpA DNA fragment. The size of the DNA standards are shown on the left side of the gel and the size of hybridizing fragment is shown on the right side of the gel.
(B) Southern Blot analysis of the wild type (WT) and mptpA mutant (MT1 and MT2) strains of *M. tuberculosis*.
Genomic DNAs (3 µg) from the wild type (WT) and mptpA mutant strain (MT1 and MT2) of *M. tuberculosis* were digested with Pvu II, separated on 1.2% agarose gel, transferred to Hybond N membrane and probed with $^{32}$P labeled mptpA DNA fragment. The size of the DNA standards are shown on the left side of the gel and the size of hybridizing fragment is shown on the right side of the gel.

(C) Immunoblot analysis of expression of MptpA in the wild type (WT) and mptpA mutant (MT1 and MT2) strains of *M. tuberculosis*.

Analysis of expression of MptpA in the wild type and mptpA mutant strain of *M. tuberculosis* by immunoblotting. The strains were grown in 7H9 media to mid-log phase. Equal amounts of whole cell lysate protein (40 μg) was resolved on 12.5% SDS-PAGE, transferred to Hybond C Extra membrane and expression of MptpA was analysed by using polyclonal sera raised against MptpA in rabbits.

Figure 2:
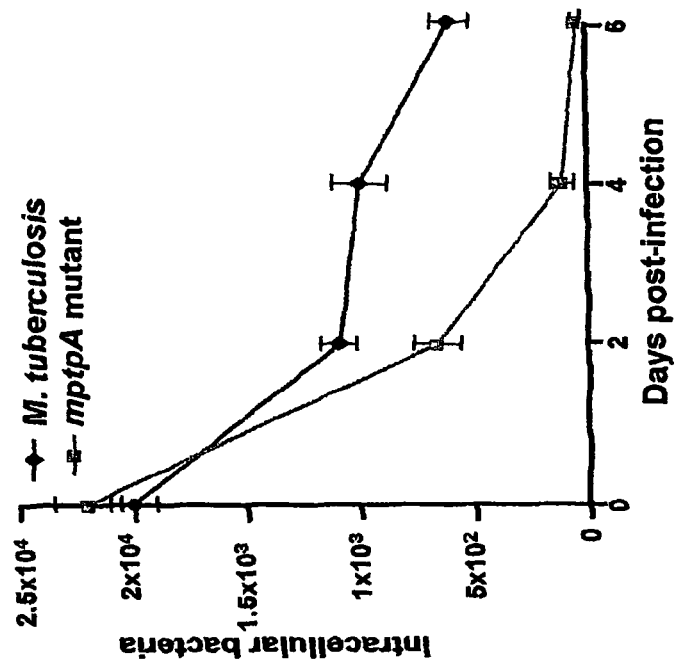
Figure 2:
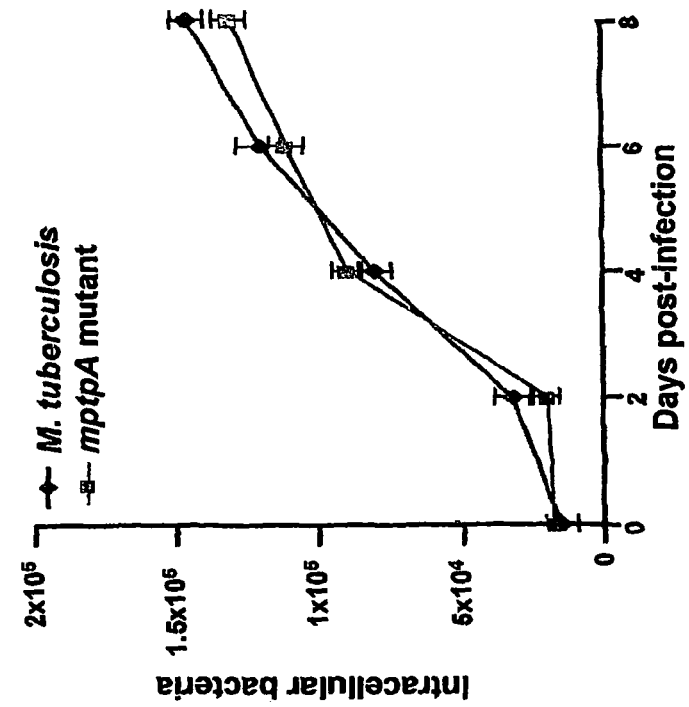

FIG. 2: Survival of the wild type and mptpA mutant strains of *M. tuberculosis* in resting and activated macrophages.

The mouse macrophage cell line J774A.1 was infected with the wild type and mptpA mutant strain of *M. tuberculosis* separately at an MOI of 1:10 (macrophage: bacilli). At different time points post-infection (day 0, 2, 4, 6 and 8), macrophages were lysed and the number of intracellular mycobacteria was assessed by plating on 7H10 plates (A—in resting macrophages, B—in activated macrophages). The experiments were carried out twice in duplicates and data is depicted as mean of all four values±S.E.

Figure 3:
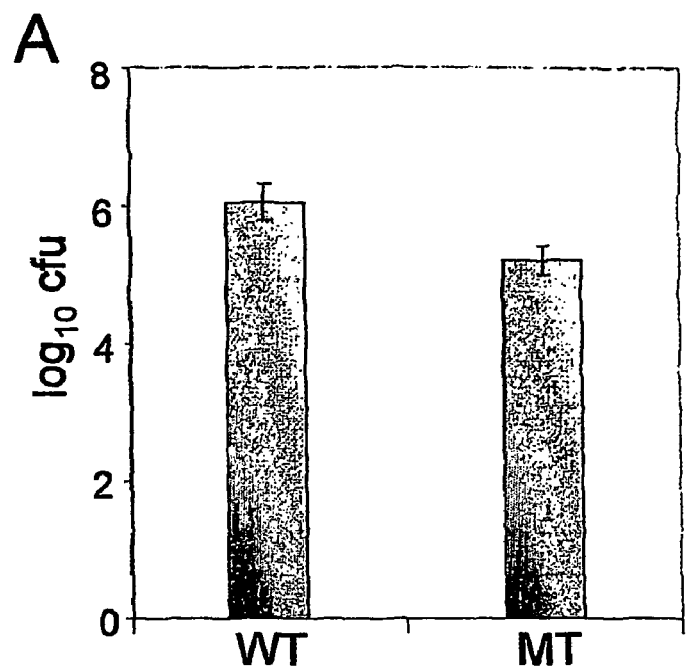
Figure 3:
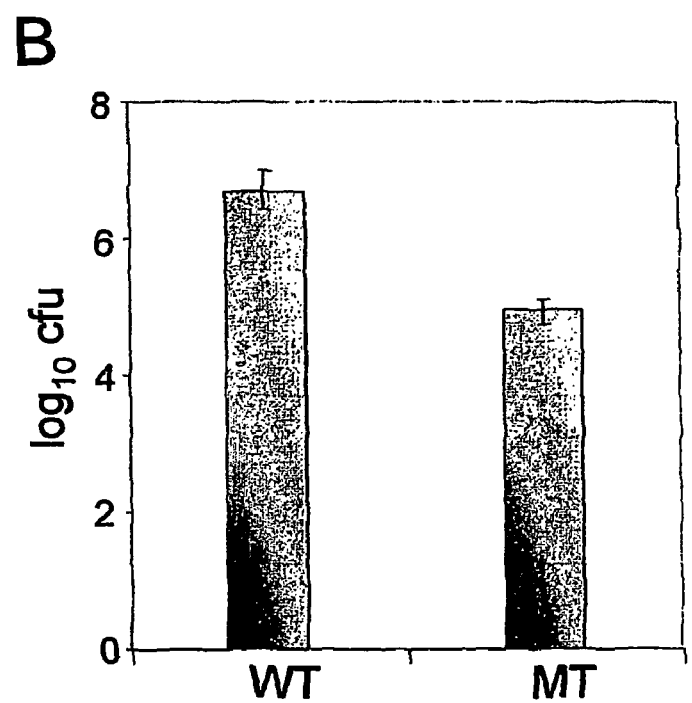

FIG. 3: Bacterial load in spleens of animals infected subcutaneously with $5 \times 10^7$ cfu of either the wild type (WT) or mptpA mutant (MT) of *M. tuberculosis* and euthanised at 3 weeks (A) and 6 weeks (B) post-infection.

Spleens were homogenized in 5 ml of distilled water and ten-fold serial dilutions of the spleen homogenates were plated in duplicates on LJ slopes. Splenic bacillary load of animals euthanised at 3 weeks (A) and 6 weeks (B) post-infection was determined, converted to $\log_{10}$ cfu and depicted as mean±S.E on y-axis. Various mycobacterial strains are depicted on the x-axis.

Figure 4:
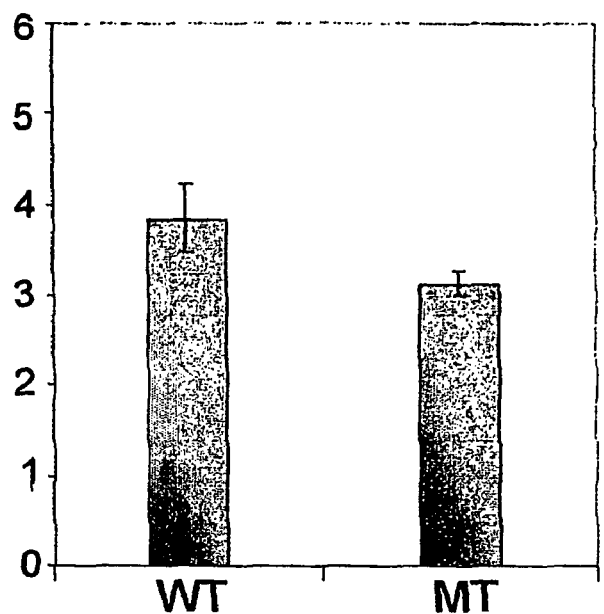
Figure 4:
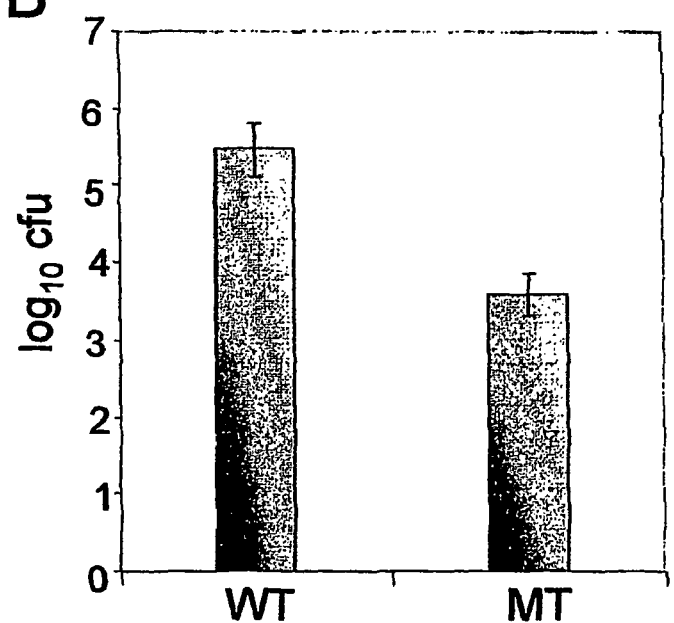

FIG. 4: Bacterial load in lungs of animals infected subcutaneously with $5 \times 10^7$ cfu of either the wild type (WT) or mptpA mutant (MT) of *M. tuberculosis* and euthanised at 3 weeks (A) and 6 weeks (B) post-infection.

A portion of lungs were homogenized in 5 ml of distilled water and ten-fold serial dilutions of the lung homogenates were plated in duplicates on LJ slopes. Lung bacillary load of animals euthanised at 3 weeks (A) and 6 weeks (B) post-infection was determined, converted to $\log_{10}$ cfu and depicted as mean±S.E on y-axis. Various mycobacterial strains are depicted on the x-axis.

Figure 5:
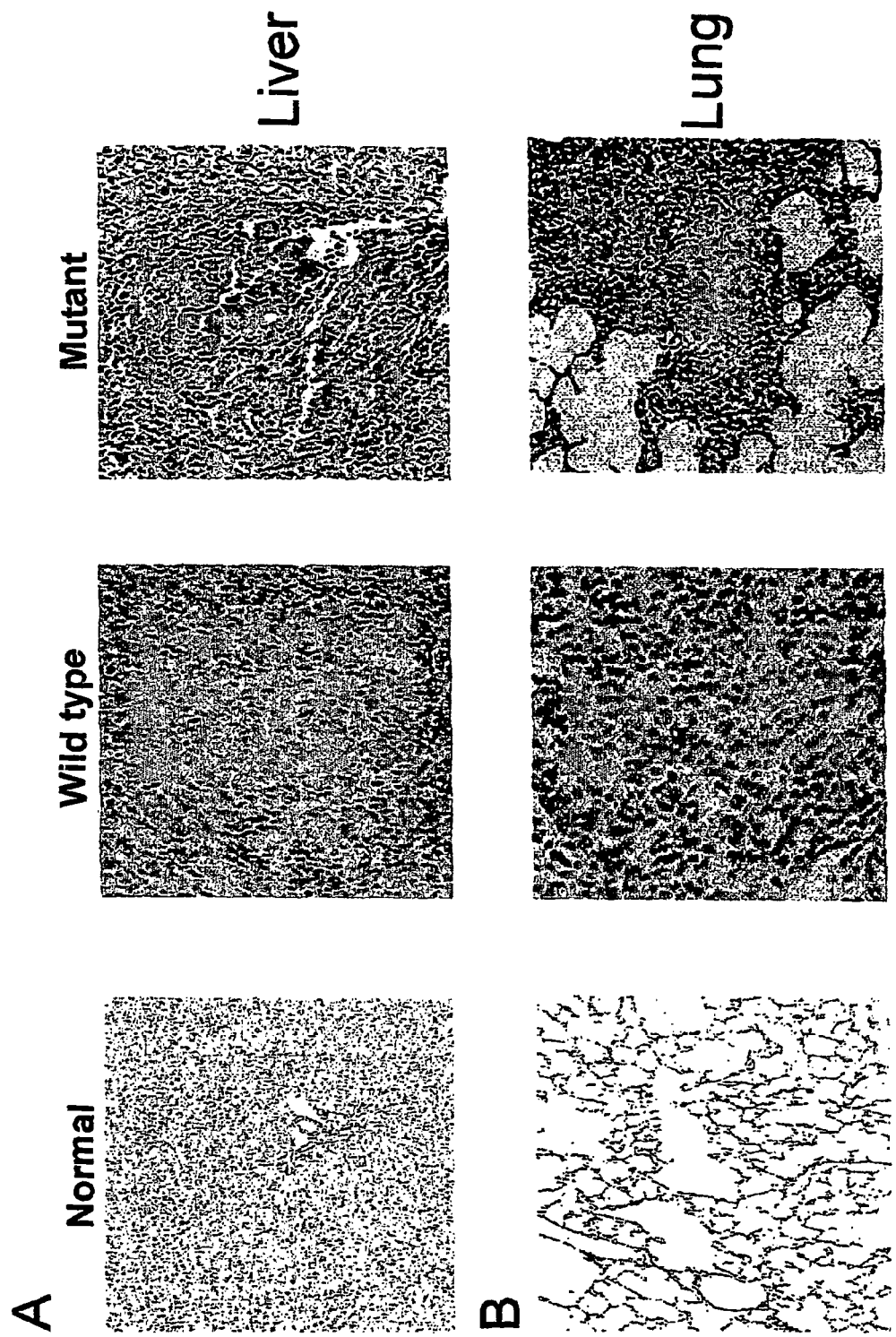

FIG. 5: Histopathology of liver and lung from guinea pigs infected subcutaneously with $5 \times 10^7$ cfu of either the wild type (WT) or mptpA mutant (MT) of *M. tuberculosis* and euthanised 3 weeks post-infection.

Portions of liver and lungs were removed under aseptical conditions and fixed in 10% formalin. Five-micron sections of tissues were stained with haematoxylin and eosin and subjected to histopathological analysis at a magnification of 10×. Representative sections of liver (A) and lung (B) from all the three groups of animals are shown. Sections of liver and lung from uninfected guinea pig were used as reference for normal tissue histology.

Figure 6:
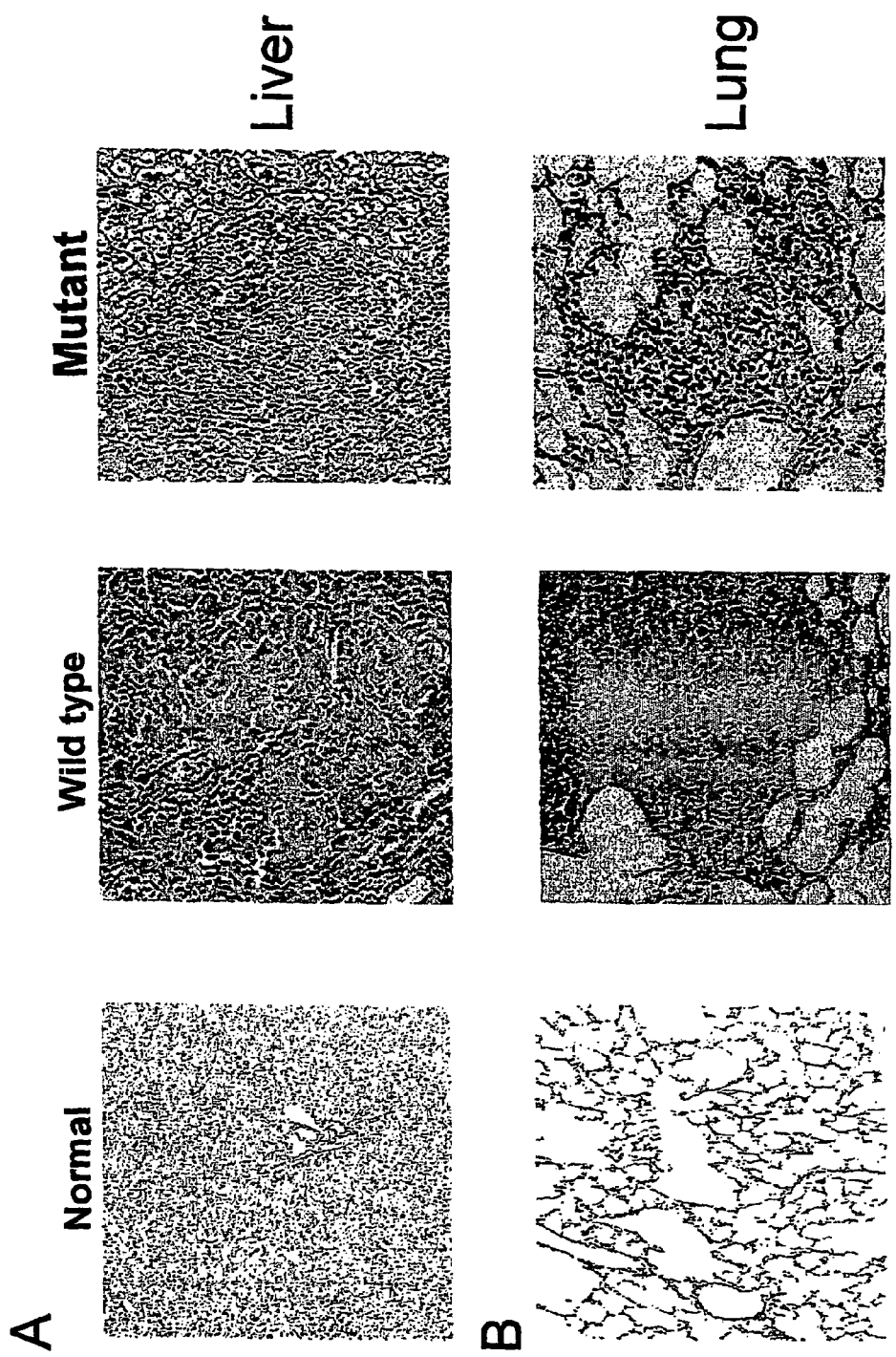

FIG. 6: Histopathology of liver and lung from guinea pigs infected subcutaneously with $5 \times 10^7$ cfu of either the wild type (WT) or mptpA mutant (MT) of *M. tuberculosis* and euthanised at 6 weeks post-infection.

Sections (5 μm) of liver and lung from animals infected with the wild type, mptpA mutant and complemented strains of *M. tuberculosis* were fixed, processed, stained with haematoxylin and eosin and observed under microscope at a magnification of 10×. Representative sections of liver (A) and lung (B) from all the three groups of animals are shown.

Sections of liver and lung from uninfected guinea pig were used as reference for normal tissue histology.

Figure 7:
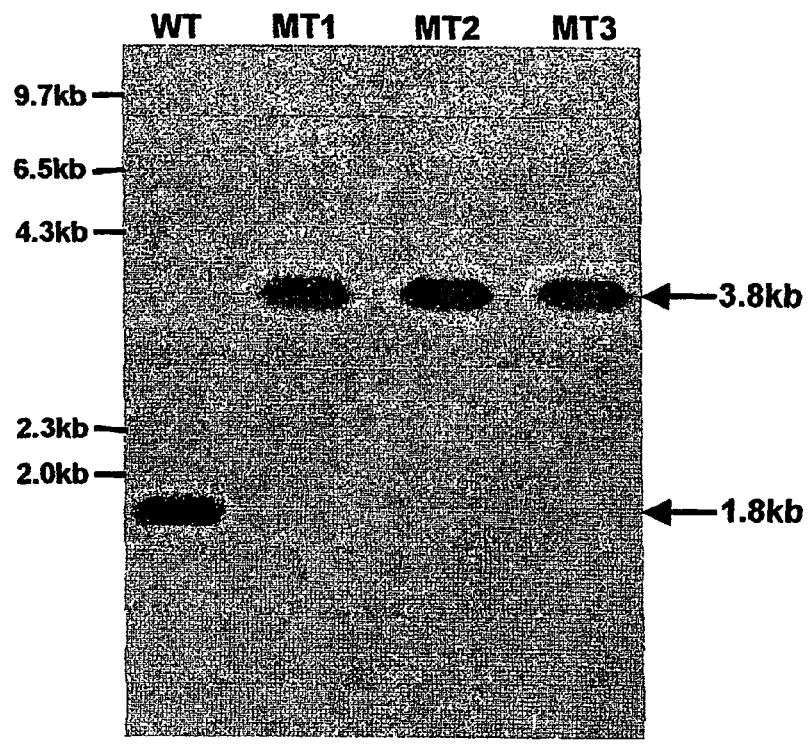
Figure 7:
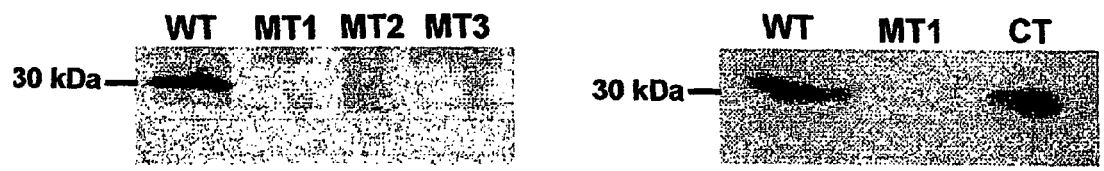

FIG. 7: (A) Southern blot analysis of the wild type and mptpB mutant strains (MT1, MT2 and MT3) of *M. tuberculosis*.

Genomic DNAs (3 μg) from wild type (WT) and mptpB mutant strain (MT1, MT2 and MT3) of *M. tuberculosis* was digested with Not I, separated on 1.2% agarose gel, transferred to Hybond N membrane and probed with $^{32}$P labeled mptpB DNA fragment. The size of DNA standards are shown on the left side of the gel and size of hybridizing band on the right side of the gel.

(B) Immunoblot analysis of the expression of MptpB in wild type (WT) and mptpB mutant (MT1, MT2 and MT3) strains of *M. tuberculosis*.

Analysis of the expression of MptpB in wild type and mptpB mutant strain of *M. tuberculosis* by immunoblotting. The strains were grown in 7H9 media to mid-log phase. Equal amounts of whole cell lysate protein (40 μg) was resolved on 12.5% SDS-PAGE, transferred to Hybond C Extra membrane, the blot was probed for the expression of MptpB using polyclonal sera raised against MptpB in rabbits.

Figure 8:
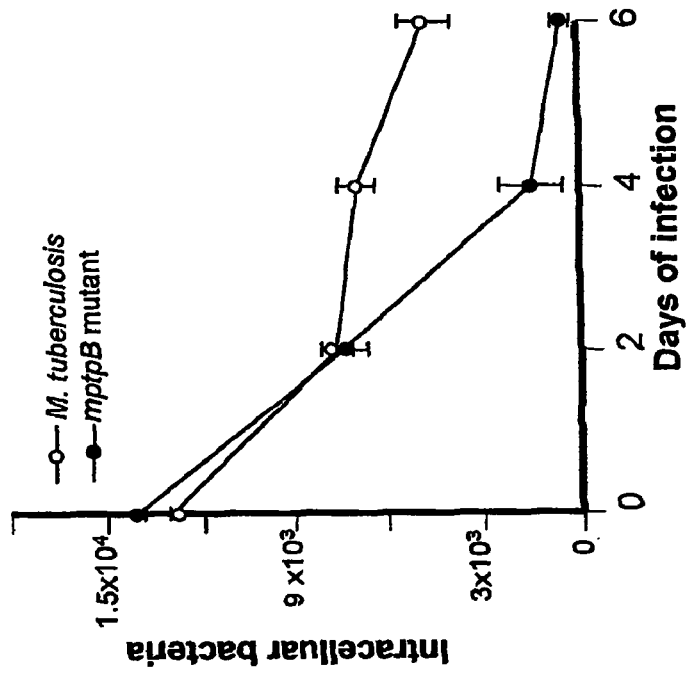
Figure 8:
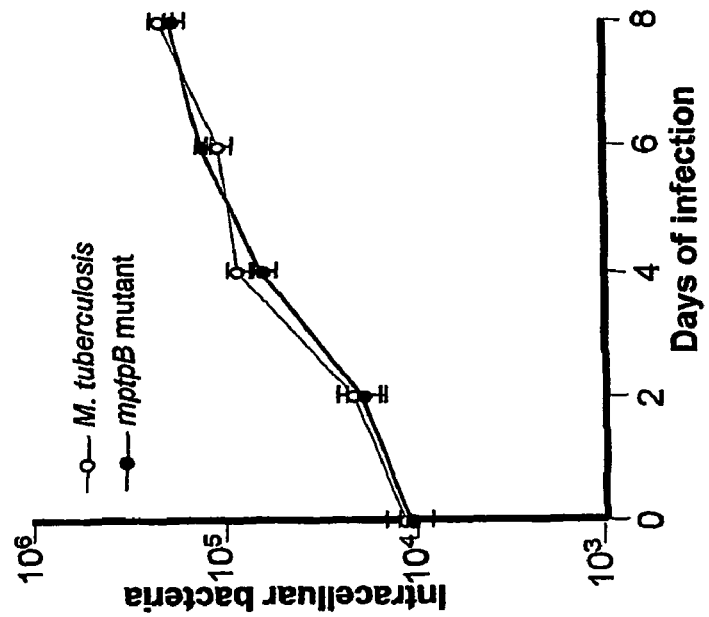

FIG. 8: Survival of wild type and mptpB mutant strains of *M. tuberculosis* in macrophages.

The mouse macrophage cell line J774A.1 was infected separately with wild type and mptpB mutant strain of *M. tuberculosis* at an MOI of 1:10 (macrophage: bacilli). At different time points post-infection (day 0, 2, 4, 6 and 8), macrophages were lysed and the number of intracellular mycobacteria was assessed by plating on MB7H10 plates (A—in resting macrophages, B—in activated macrophages). The experiments were carried out twice in duplicates and data is depicted as mean of all four values±S.E.

Figure 9:
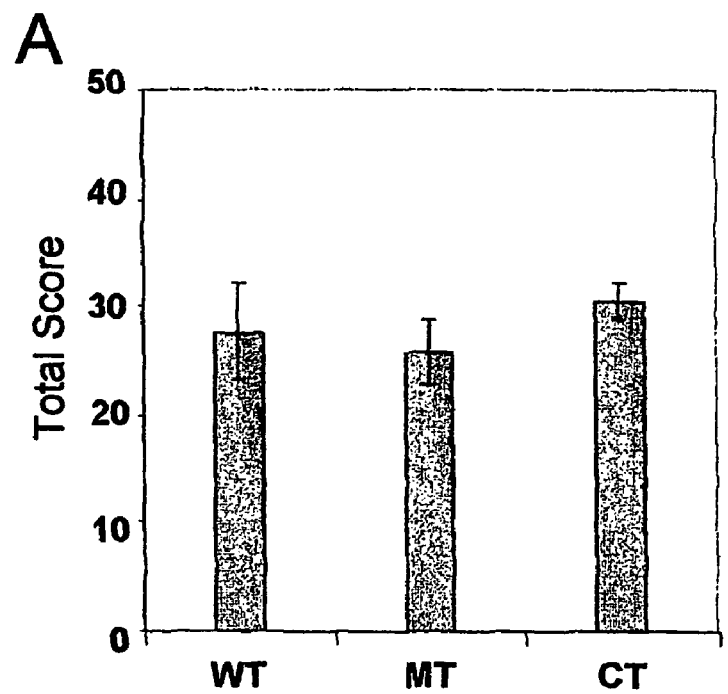
Figure 9:
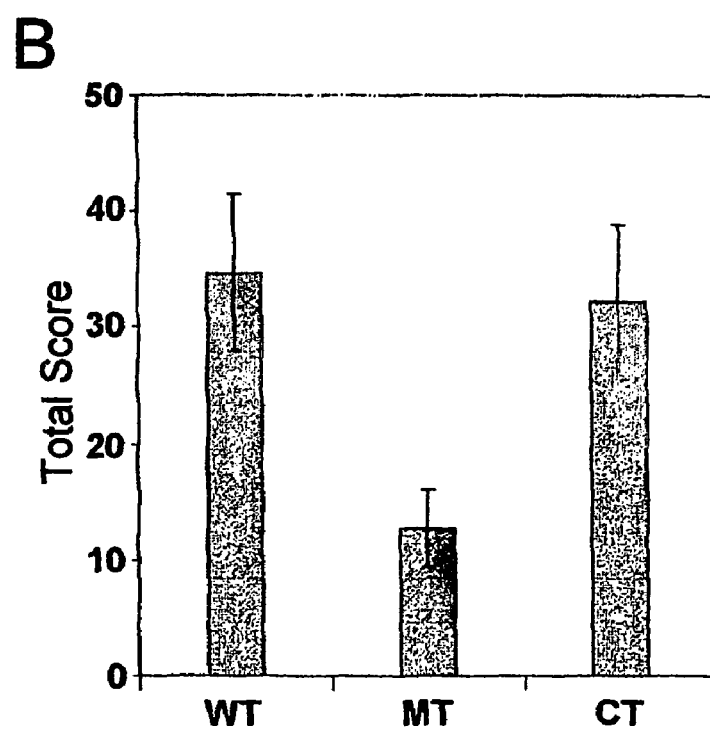

FIG. 9: Total post mortem score of guinea pigs infected with $5 \times 10^5$ cfu of wild type (WT), mptpB mutant (MT) and complemented strain (CT) and euthanised at 3 weeks (A) and 6 weeks (B) post-infection.

At the time of sacrifice, depending on the magnitude of pathological damage in spleen, liver, lung, lymph nodes and sites of injection, scores were assigned to each organ as described by Mitchison. Total score for each animal was obtained by totaling up the scores obtained for individual organs and is depicted as mean±S.E on y-axis. Various mycobacterial strains are depicted on x-axis.

Figure 10:
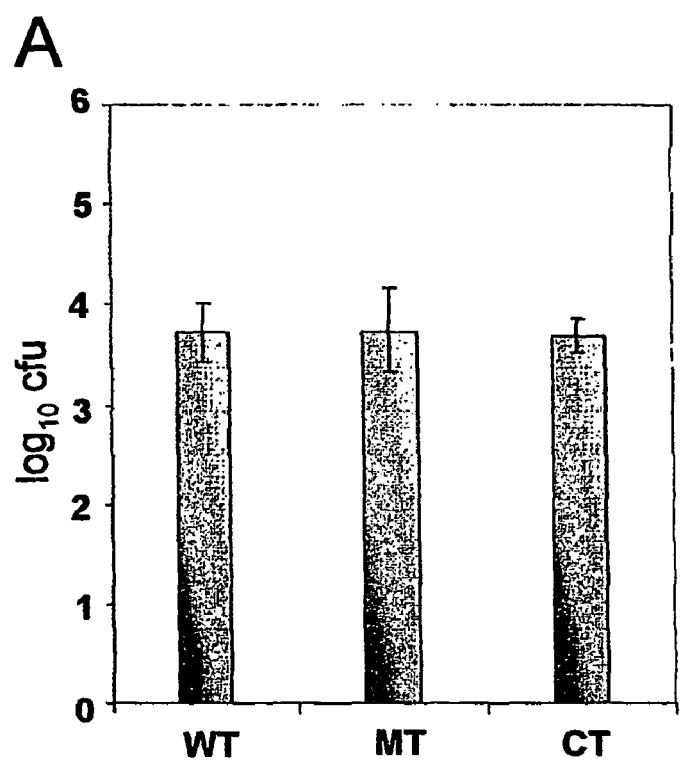
Figure 10:
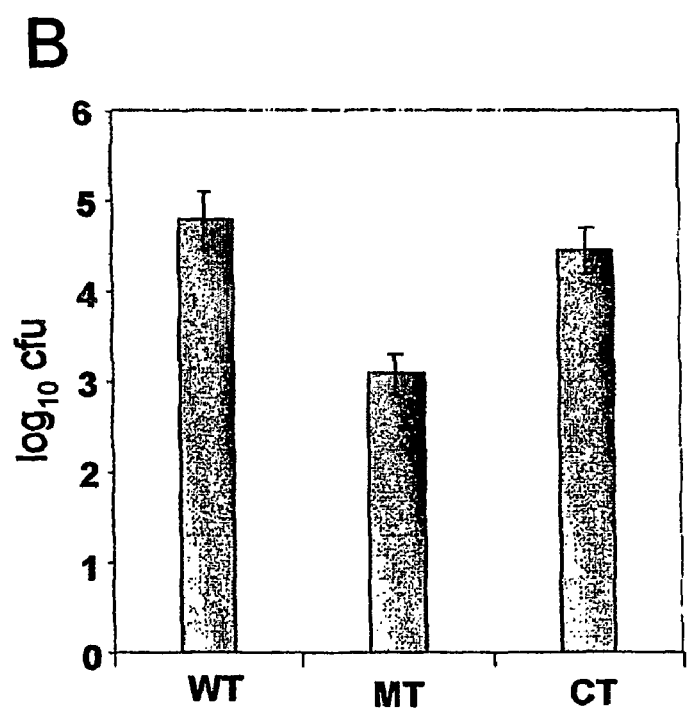

FIG. 10: Bacterial load in spleens of guinea pigs infected with $5 \times 10^5$ cfu of either wild type (WT), mptpB mutant (MT) or complemented strain (CT) of *M. tuberculosis* and euthanised 3 weeks (A) and 6 weeks (B) post-infection.

Spleens were homogenized in 5 ml of distilled water and ten-fold serial dilutions of the spleen homogenates were plated in duplicates on LJ slopes. Splenic bacillary load of animals euthanised 3 weeks (A) and 6 weeks (B) post-infection was determined, converted to $\log_{10}$ cfu and depicted as mean±S.E on y-axis. Various mycobacterial strains are depicted on the x-axis.

Figure 11:
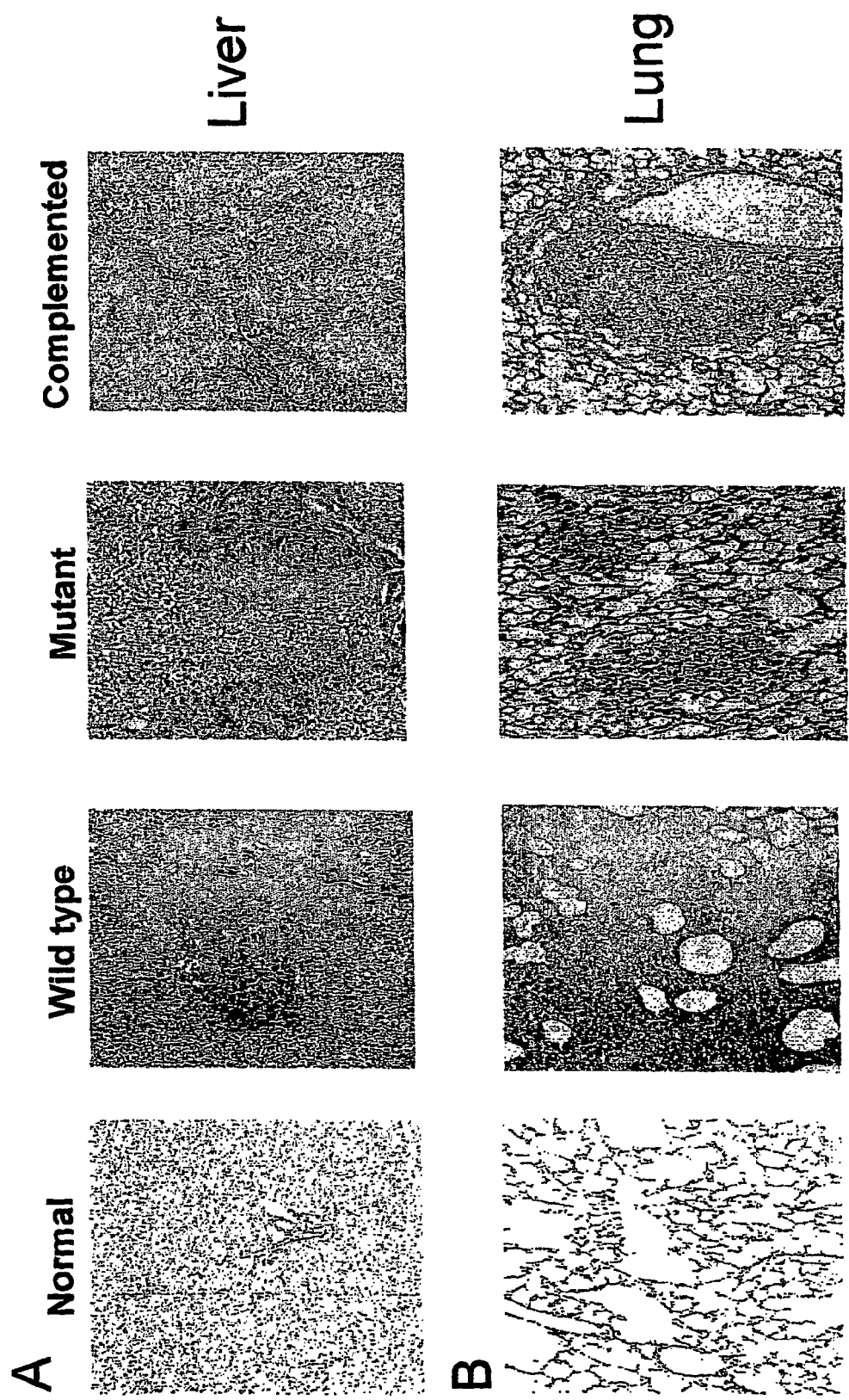

FIG. 11: Histopathology of liver and lung from guinea pigs infected with $5 \times 10^5$ cfu of either wild type, mptpB mutant or complemented strain of *M. tuberculosis* and euthanised at 3 weeks post-infection.

Portions of liver and lungs were removed under aseptical conditions and fixed in 10% formalin. Five-micron sections of tissues were stained with haematoxylin and eosin and subjected to histopathological analysis at a magnification of 10×. Representative sections of liver (A) and lung (B) from all the three groups of animals are shown. Sections of liver and lung from uninfected guinea pig were used as reference for normal tissue histology.

Figure 12:
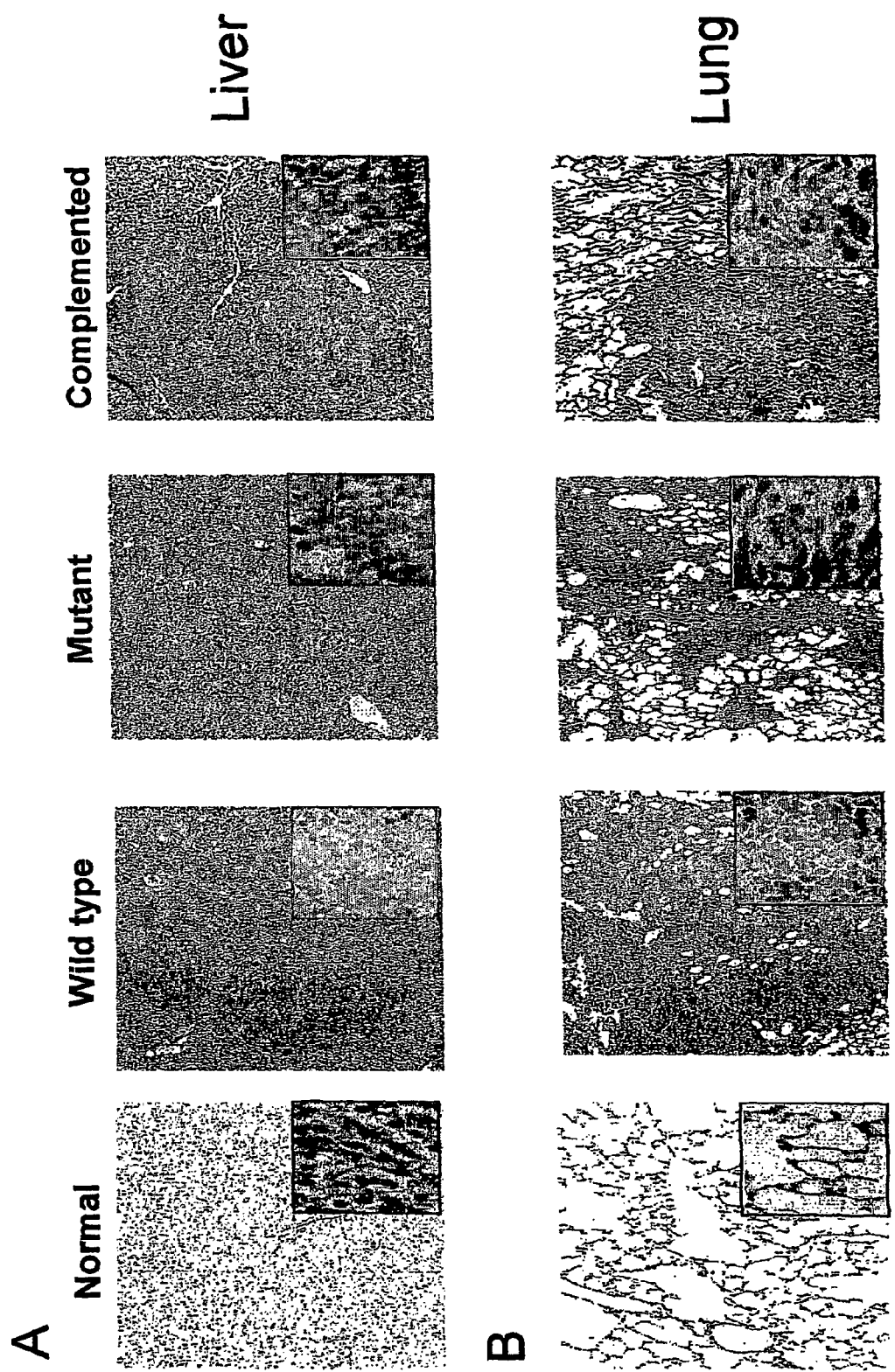

FIG. 12: Histopathology of liver and lung from guinea pigs infected with 5×10⁵ cfu of either wild type, mptpB mutant or complemented strain of *M. tuberculosis* and euthanised at 6 weeks post-infection.

Sections (5 μm) of liver and lung from animals infected with wild type, mptpB mutant and complemented strains of *M. tuberculosis* were fixed, processed, stained with haematoxylin and eosin and observed under microscope at a magnification of 10×. Representative sections, with an inset of high magnification (20×), of liver (A) and lung (B) from all the three groups of animals are shown. Sections of liver and lung from uninfected guinea pig were used as reference for normal tissue histology.

DETAILED DESCRIPTION OF THE INVENTION

The present invention provides a *Mycobacterium* strain with a modified tyrosine phosphatase gene in its genome, wherein the said *Mycobacterium* strain is incapable of expressing the active tyrosine phosphatase gene. Further the *Mycobacterium* species is selected from a group consisting of *M. tuberculosis* and *M. bovis*.

The invention provides a *Mycobacterium* strain wherein the modified tyrosine phosphatase gene is either modified mptpA or mptpB gene. The modified mptpA gene is as shown in SEQ ID NO: 15. and the modified mptpB gene is as shown in SEQ ID NO: 16.

The invention further provides a recombinant vector comprising the modified mptpA or mptpB gene. Further, the recombinant vector constructed is either pAKΔA or pBKΔB.

Another aspect of the invention relates to a recombinant vector, wherein the nucleotide sequence of mptpA gene is as shown in SEQ ID NO: 11 is modified. Further, the invention relates to a recombinant vector, wherein the nucleotide sequence of mptpB gene is as shown in SEQ ID NO: 12 is modified.

The invention provides the recombinant vector, wherein the mptpA or mptpB gene is modified by insertion, deletion, mutation or substitution.

Further, the invention specifically provides a recombinant vector, wherein the mptpA or mptpB gene is modified by substituting an internal region of the mptpA or mptpB gene by an antibiotic resistance marker gene which can be used for selection.

Another aspect of the invention provides a recombinant vector, wherein the antibiotic resistance marker gene imparts resistance to either hygromycin or chloramphenicol preferably to hygromycin.

Further the present invention provides a recombinant vector containing a second antibiotic marker gene for kanamycin resistance in the backbone of the said recombinant vector.

The invention provides both the wild type nucleic acid sequences and the modified forms of the tyrosine phosphatase genes. The invention provides nucleotide sequence of the mptpA gene encoding the mycobacterial tyrosine phosphatase A as shown in SEQ ID NO: 11 and modified mptpA gene as shown in SEQ ID NO: 15. The invention provides nucleotide sequence of the mptpB gene encoding the mycobacterial tyrosine phosphatase B as shown in SEQ ID NO: 12 and modified mptpB gene as shown in SEQ ID NO: 16.

Another embodiment of the invention is for a method of developing a mutant *Mycobacterium* strain with a modified tyrosine phosphatase gene in its genome comprising the following steps:
a. extracting genomic DNA from *Mycobacterium* strain,
b. amplifying the tyrosine phosphatase gene along with the flanking sequences using specific primers from the genomic DNA of step (a) to obtain a DNA fragment,
c. characterizing the fragment of step (b),
d. cloning the fragment of step (b) in a non-replicative vector,
e. modifying the fragment in the non-replicative vector of step (d),
f. inserting an antibiotic resistance marker gene within the fragment of step (e) to obtain a non-replicative vector containing a modified tyrosine phosphatase gene,
g. cloning of a second antibiotic resistance marker gene in the backbone of the non-replicative vector of step (f), to obtain a recombinant vector,
h. introducing the recombinant vector of step (g) into *Mycobacterium* strains,
i. selecting for primary recombinant *Mycobacterium* strains using first antibiotic selection marker gene,
j. culturing the primary recombinant *Mycobacterium* strains of step (i) harboring the first antibiotic resistance marker gene,
k. selecting the secondary recombinant *Mycobacterium* strains of step (j) that is sensitive to the second antibiotic resistance gene present in the vector backbone,
l. culturing the secondary recombinant *Mycobacterium* strains of step (k), wherein the said recombinant *Mycobacterium* strain harboring the modified tyrosine phosphatase gene which shows defective growth in activated macrophages and animals.

Further, the invention provides a method wherein, the *Mycobacterium* species is selected from a group consisting of *M. tuberculosis* and *M. bovis*

Another aspect of the invention provides a method wherein the specific primers are selected from a group comprising of SEQ ID NO: 1 to 4 for amplification of mptpA along with its flanking regions and SEQ ID NO: 5 to 8 for amplification of mptpB along with its flanking regions.

The invention further provides a method, wherein the mptpA or mptpB gene is modified by insertion, deletion, mutation or substitution specifically by substituting an internal region of the mptpA or mptpB gene by an antibiotic resistance marker gene preferably hygromycin resistance gene.

The invention provides a method, wherein in the second antibiotic marker gene imparting resistance to kanamycin is inserted in the recombinant vector backbone.

Yet another aspect of the invention is to modify tyrosine phosphatase gene in the genome of *Mycobacterium* using either recombinant vector pAKΔA or pBKΔB.

The present invention further provides a method wherein homologous recombination may be used to replace the active tyrosine phosphatase gene of mycobacteria by a double cross over event with a modified gene to develop a mutant *Mycobacterium* strain.

Another embodiment of the invention is to assess the role of MptpA and MptpB in the virulence and pathogenesis of mycobacteria in activated macrophages and animals.

Further the invention shows that the mutant *Mycobacterium* strains are attenuated and impaired in their ability to survive in activated macrophages and animals.

Further the invention relates to two tyrosine phosphatases MptpA and MptpB of mycobacteria which are potential targets for developing anti-tubercular drugs.

(A) Construction of Recombinant Vector, pAKΔA.

The mutant strain lacking tyrosine phosphatases associated with either MptpA was employed to understand the role of these proteins in the survival of *M. tuberculosis* in murine macrophages and in the ability of the mutants to cause disease in guinea pigs.

The wild type tyrosine phosphatase gene was modified to develop a mutant strain of *Mycobacterium*. The genome of *Mycobacterium* encodes for two tyrosine phosphatase, MptpA and MptpB. The genomic DNA from *mycobacterium* strain was extracted by CTAB standard methods as given in Example 3. The gene for mptpA was amplified from the genome using specific primers as shown in Table 1 and also given in Example 4.

Based on the genome sequence of *M. tuberculosis*, the primers were designed to amplify mptpA (SEQ ID NO: 11) along with its upstream and downstream flanking regions. A DNA fragment carrying 1135 bp upstream to the mptpA ORF along with the initial 156 bp of mptpA ORF was PCR amplified by using *M. tuberculosis* DNA as template and primer A (SEQ ID NO: 1) and primer B (SEQ ID NO: 2) carrying a Nde I site at the 5' end. The amplicon was end-repaired and cloned into EcoR V digested vector pLitmus-38 resulting in vector pLitA1. The ligation was transformed into *E. coli* as given in Example 5. The plasmids were isolated from the recombinants as given in Example 6. The recombinants were analysed by restriction enzyme digestion as given in Example 7.

Another DNA fragment carrying 167 bp of mptpA ORF corresponding to the C-terminal region of MptpA along with 1240 bp downstream to the mptpA ORF was PCR amplified by using gene specific primers, primer C (SEQ ID NO: 3) carrying a Nde I site at the 5' end and primer D (SEQ ID NO: 4) carrying a BspH I site at the 5' end. The amplicon was end-repaired and separately cloned into EcoR V digested vector pLitmus-38 resulting in vector pLitA2. The vector pLitA1 was digested with Nde I and Sca I and the larger DNA fragment containing the initial 156 bp of mptpA ORF along with 1135 bp upstream to the mptpA ORF was gel purified by standard procedure as given in Example 8 and 9. Similarly, vector pLitA2 was digested with Nde I and Sca I and the smaller DNA fragment containing the 167 bp of mptpA ORF corresponding to the C-terminal region of MptpA along with 1240 bp downstream to the mptpA ORF was gel purified. The larger fragment obtained by the digestion of pLitA1 and the smaller fragment obtained by the digestion of pLitA2 were then ligated together resulting in pLitΔA. The mptpA specific primers primer B (SEQ ID NO: 2) and primer C (SEQ ID NO: 4) were non-overlapping; as a result, the vector pLitΔA contained the coding region of mptpA with a deletion of 112 bp from the central region of ORF. The vector pLitΔA comprises nucleotide sequence as shown in SEQ ID NO: 13. The insert sequence in the vector was characterized by sequencing as shown in Example 11.

The vector also carried 1135 bp of upstream and 1240 bp of downstream flanking sequences and a unique Nde I site in the ORF of mptpA at the deletion site for the cloning of hygromycin resistance gene. The hygromycin resistance gene was excised out from pLit28res-hyg-res as a BamH I-Xba I fragment, end-repaired and cloned into Nde I digested, end-repaired pLitΔA resulting in pLitΔAH. The insert sequence in the vector was characterized by sequencing as shown in Example 11. The vector pLitΔAH comprises an insert having nucleotide sequence as shown in SEQ ID NO: 15.

A 4.8 kb DNA fragment containing mptpΔA::hyg$^r$ was excised out from pLitΔAH as a Spe I-Nhe I fragment and cloned into Xba I —digested pJQ200SK (a non-replicative suicide vector) yielding pJQΔA. A second antibiotic resistance marker for kanamycin resistance was inserted in the vector backbone as given below.

The gene conferring resistance to kanamycin was excised out from pSD5 as an Nhe I-BstE II fragment, end repaired and cloned into Sma I digested pJQΔA resulting in pAKΔA. The recombinant vector pAKΔA provided 1.3 kb and 1.4 kb homologous region on either side of the hygromycin resistant gene for recombination to occur at mptpA locus between targeting DNA and the mycobacterial genome.

The recombinant vector pAKΔA comprises the modified mptpA gene (SEQ ID NO 15) and a second antibiotic resistance marker in the backbone.

(B) Construction of Recombinant Vector pBKΔB.

For disruption of mptpB of *M. tuberculosis*, vector pBKΔB was constructed. The genomic DNA from *mycobacterium* strain was extracted by CTAB standard methods as given in Example 3. The gene for mptpB (SEQ ID NO: 12) was amplified from the genome using specific primers as shown in Table 1 and also given in Example 4.

Based on the genome sequence of *M. tuberculosis*, the primers were designed to amplify mptpB (SEQ ID NO: 12) along with its upstream and downstream flanking regions. For this, a DNA fragment containing 1045 bp upstream to the ORF of mptpB along with the initial 356 bp of ORF of mptpB was PCR amplified using *M. tuberculosis* DNA as template and primers E (SEQ ID NO: 5) and primer F (SEQ ID NO: 6). The amplicon was end-repaired and cloned into Eco R V digested vector pLitmus-38 resulting in vector pLitB1. The ligation was transformed into *E. coli* as given in Example 5. The plasmids were isolated from the recombinants as given in Example 6. The recombinants were analysed by restriction enzyme digestion as given in Example 7.

Another DNA fragment containing 367 bp of mptpB ORF corresponding to the C-terminal region of MptpB along with 1140 bp downstream to the ORF of mptpB was PCR amplified using gene specific primers primer G (SEQ ID NO: 7) and primer H (SEQ ID NO: 8). The amplicon was end-repaired and separately cloned into EcoR V digested vector pLitmus-38 resulting in vector pLitB2. The vector pLitB1 was digested with Nde I and Sca I and the larger DNA fragment containing the initial 356 bp of mptpB ORF along with 1045 bp upstream to the ORF was gel purified using a Qiagen gel extraction kit. Similarly, pLitB2 was digested with Nde I and Sca I and the smaller DNA fragment containing the 367 bp of mptpB ORF corresponding to the C-terminal region of MptpB along with 1140 bp downstream to the ORF was gel purified. The larger fragment obtained by the digestion of pLitB1 and the smaller fragment obtained by the digestion of pLitB2 were then ligated together resulting into pLitΔB. The mptpB specific primers primer F (SEQ ID NO: 6) and primer G (SEQ ID NO: 7) were non-overlapping, as a result, the vector pLitΔB contained the coding region of mptpB (with a deletion of 108 bp from the central region of ORF) and 1045 bp of upstream and 1140 bp of downstream flanking sequences and a unique Nde I site in the ORF of mptpB at the deletion site for the cloning of hygromycin resistance gene cassette. The vector pLitΔB comprises nucleotide sequence as shown in SEQ ID NO: 14. The insert sequence in the vector was characterized by sequencing as shown in Example 11.

The hygromycin resistance gene cassette was excised out from pLit28res-hyg-res as a BamH I-Xba I fragment, end-repaired and cloned into Nde I digested, end-repaired pLitΔB resulting in pLitΔBH. The insert sequence in the vector was characterized by sequencing as shown in Example 11. The vector pLitΔBH comprised the insert having nucleotide sequence as shown in SEQ ID NO: 16.

A 4.9 kb DNA fragment containing mptpΔB::hyg$^r$ was excised out from pLitΔBH as a Spe I-Nhe I fragment and cloned into Xba I —digested pJQ200SK (a non-replicative suicide vector, Pelicic et al., 1996) yielding pJQΔB. A second antibiotic resistance marker for kanamycin resistance was inserted in the vector backbone as given below.

The gene conferring resistance to kanamycin was excised out from pSD5 as an Nhe I-BstE II fragment, end repaired and cloned into Sma I-digested pJQΔB resulting in pBKΔB. The vector pBKΔB provided 1.4 kb and 1.5 kb homologous regions upstream and downstream of the hygromycin resistant gene, respectively, for recombination to occur between targeting DNA and the mycobacterial genome.

The recombinant vector pBKΔB comprises the modified mptpB gene (SEQ ID NO: 16) and as second resistance marker in the backbone.

(C) Modification of the mptpA in the Genome of *Mycobacterium* and its Role in the Virulence and Pathogenesis of *M. tuberculosis*.

In order to evaluate the role of MptpA in the pathogenesis of *M. tuberculosis*, an mptpA mutant strain was constructed by using a non-replicative vector pAKΔA having modified mptpA sequence as shown in SEQ ID NO: 15. The recombinant vector, pAKΔA carried the coding region of mptpA along with it's 1135 bp upstream and 1240 bp downstream flanking sequences of mptpA. A portion of the coding region (112 bp) of MptpA was deleted and replaced with gene conferring resistance to hygromycin in pAKΔA. Electroporation of *M. tuberculosis* Erdman with non-replicative vector, pAKΔA and alkali denatured pAKΔA resulted in 39 and 2 hygromycin resistant transformants, respectively on 7H10 plates supplemented with hygromycin (50 μg/ml). The details are of electroporation are given in Example 12. The alkali pretreatment is as given in Example 13. All the transformants were PCR positive for hygromycin resistance gene suggesting that plasmid borne mptpΔA::hyg$^r$ had integrated in the mycobacterial genome. Allelic exchange by homologous recombination should result in incorporation of the hygromycin resistance gene but not the vector backbone (carrying kanamycin resistance gene) into the mycobacterial genome. Thus, the transformants were screened for kanamycin resistance gene by PCR using gene specific primers. The transformants obtained upon electroporation of pAKΔA were PCR positive for the kanamycin cassette, where as the two transformants obtained upon electroporation of alkali denatured pAKΔA were PCR-negative for the kanamycin cassette. These results indicated that homologous recombination at mptpA locus had occurred in the case of transformants obtained upon electroporation of alkali denatured DNA. Thus, transformants resistant to hygromycin but sensitive to kanamycin were selected to score for homologous recombination event.

The disruption of mptpA in the mycobacterial genome was verified by Southern blot analysis using mptpA specific DNA probe (SEQ ID NO: 11). The details of the southern blot hybridization and preparation of nucleic acid probes are given in Example 14 and 15). As expected, for allelic exchange event to occur at homologous site, in the lanes corresponding to the two hyg$^r$ kan$^s$ transformants, a single hybridizing fragment 4.1 kb, 2 kb longer than that in the wild type strain (2.1 kb) was observed. This increase in the size of the band by 2.0 kb in both hyg$^r$ kan$^s$ transformants corresponded to the replacement of 112 bp internal fragment of mptpA with hygromycin resistance gene (FIG. 1A). Immunoblot analysis (as given in Example 10) of whole cell lysate demonstrated that disruption of mptpA resulted in lack of expression of MptpA in the mutant strain (FIG. 1B).

To investigate the role of MptpA in the intracellular survival of *M. tuberculosis*, the survival rates of mptpA mutant and its parental strain were compared in resting as well as in IFN-γ activated mouse macrophage cell line, J774A.1. The numbers of intracellular surviving bacteria were calculated at days 0, 2, 4, 6 and 8 post-infection. Both parental as well as mptpA mutant strain displayed a similar pattern of intracellular growth in resting macrophages. While at the initial time point (day0) bacillary counts were approximately $2\times10^4$ per well. The bacillary load increased at later time points attaining peak values of $2\times10^5$ at day 8 post-infection. These results showed that both parental as well as mptpA mutant strains of *M. tuberculosis* exhibited comparable capacity of infection and multiplication in resting macrophages (FIG. 2A). However, both the strains differed in their ability to survive in IFN-γ activated macrophages. In activated macrophages approximately 45%, 50% and 70% killing of wild type bacilli was observed, at days 2, 4 and 6 post-infection, respectively, in comparison to 70%, 95% and 98% killing of mptpA mutant strain at days 2, 4 and 6 post-infection, respectively (FIG. 2B). These observations indicated that disruption of mptpA had impaired the ability of *M. tuberculosis* to survive in IFN-γ activated macrophages. The details of in vitro studies in macrophages are shown in Example 16.

To determine whether MptpA plays a role in the pathogenesis of *M. tuberculosis*, guinea pigs in groups of 16 animals were infected subcutaneously with $5\times10^7$ cfu of parental, mutant or complemented strain of *M. tuberculosis*. Animals were euthanised 3 weeks and 6 weeks post-infection. At both time points of euthanisation (7 animals per group), number of colony forming units in spleen and lungs were enumerated (represented as $\log_{10}$cfu for each group).

The mptpA mutant strain was significantly attenuated for growth in guinea pig model of tuberculosis. At 3 weeks post-infection a 9-fold reduction was observed in the bacillary load in spleens of animals infected with mptpA mutant strain ($\log_{10}$ 5.09±0.23) as compared to the parental strain ($\log_{10}$ 5.99±0.27, FIG. 3A). A similar reduction in cfu was also observed in the lungs of animals infected with mptpA mutant strain, ($\log_{10}$ 3.07±0.13) as compared to ($\log_{10}$ 3.95±0.32) in the lungs of animals infected with the parental strain (FIG. 4A). The differences in the bacterial load in the spleen and lungs of animals infected with mptpA mutant strain as compared to the bacterial load of animals infected with parental strain increased from 9 folds to 90 folds at six weeks post-infection. The bacillary load in the animals infected with mptpA mutant strain was $\log_{10}$ 4.83±0.43 for spleens and 3.71±0.30 for lungs, when compared to the bacillary load in animals infected with parental strain 6.73±0.33 for spleens and 5.62±0.38 for lungs (FIGS. 3B and 4B, respectively). The reduction in the bacillary load in the spleens and lungs of animals infected with mptpA mutant strain was found to be statistically significant ($p<0.002$ in the case of spleens and $p<0.001$ in the case of lung, respectively).

Sections of liver and lung from various groups were analysed histologically to determine the extent of tissue damage. FIG. 5 depicts the mean percentage of granuloma and cellular composition in liver granuloma of animals at 3 weeks post-infection. At 3 weeks post-infection, the animals infected with the parental strain exhibited 5.4% liver granuloma. The liver granuloma comprised of 10% lymphocytes, 8% macrophages and 82% epitheloid cells. In case of animals infected with the mptpA mutant strain, 10% liver granuloma was observed and the granuloma comprised of 21% lymphocytes, 11% macrophages and 68% epitheloid cells (FIG. 5).

In case of lung, no significant difference was observed in the percentage of granulomatous tissue and cellular composition of the granuloma in case of animals infected with various strains. The animals infected with parental strain exhibited 14% lung granuloma and lung granuloma comprised of 30% lymphocytes and 70% macrophages. In case of animals infected with mptpA mutant strain 21.5% lung granuloma was observed and the granuloma comprised of 30% lymphocytes and 70% macrophages. Representative sections of liver and lung of animals infected with the parental or mptpA mutant strain at 3 weeks post-infection are shown in FIG. 6. The details of guinea pig studies is shown in Example 17.

(D) Modification of the mptpB in *M. tuberculosis* and its Effect on the Pathogenesis of *M. tuberculosis*:

In order to establish whether MptpB plays a role in the pathogenesis of *M. tuberculosis*, a mptpB mutant strain of *M. tuberculosis* was constructed by using a non-replicative suicidal vector pBKΔB having a modified mptpB sequence as shown in SEQ ID NO: 16. The targeting vector, pBKΔB carried the coding region of mptpB along with 1045 bp upstream and 1140 bp downstream flanking sequences. A portion of the coding region (108 bp) of MptpB was deleted and replaced with the gene conferring resistance to hygromycin in pBKΔB. The vector also carried the gene conferring resistance to kanamycin in its backbone as a second antibiotic selection marker for negative screening of allelic exchange events at the homologous site.

Electroporation of *M. tuberculosis* with pBKΔB and U.V. irradiated pBKΔB resulted in 22 and 3 hygromycin resistant transformants, respectively. The details of electroporation are given in Example 12. The U.V. irradiation is as given in Example 13. PCR analysis revealed that all the transformants contained hygromycin cassette indicating that these colonies were not spontaneous resistance mutants and arose from integration of the suicidal vector into the mycobacterial genome. Allelic exchange event by homologous recombination should result in the incorporation of hygromycin resistance gene but not the vector backbone (having kanamycin resistance gene) into the mycobacterial genome. Thus, transformants resistant to hygromycin but sensitive to kanamycin were selected to screen for homologous recombination event. All the transformants obtained on electroporation of untreated DNA were kanamycin resistant while the three transformants obtained on electroporation of U.V. pretreated DNA were sensitive to kanamycin. This suggested that an allelic exchange event at the homologous site had taken place in the case of these three hyg$^r$ kan$^s$ transformants obtained upon electroporation of U.V. irradiated DNA.

mptpB gene disruption was assessed by hybridization analysis of genomic DNA isolated from the parental *M. tuberculosis* strain and three hyg$^R$kan$^S$ transformants. A DNA fragment containing the entire coding region of mptpB (SEQ ID NO: 12) was used as probe as given in Example 15. Southern blot analysis (as given in Example 14) showed presence of a 1.85 kb band in the parental strain whereas a 3.8 kb band was observed in all the three hyg$^R$kan$^S$ transformants as expected upon replacement of 108 bp internal fragment of mptpB with hygromycin resistance gene cassette (FIG. 7A). These results indicated that mptpB was disrupted in all the three hyg$^R$kan$^S$ transformants. Expression of MptpB was analysed in the mutant strains using polyclonal sera raised against MptpB in rabbit. Western blot analysis (as shown in Example 10) showed absence of MptpB expression in all the three mutant strains (FIG. 7B). The complemented strain was constructed by electroporation of pSD5-mptpB into electrocompetent cells of the mutant strain. The electroporation of pSD5-mptpB restored the expression of MptpB in the complemented strain (FIG. 7B).

To study the effect of disruption of mptpB gene on the intracellular survival of *M. tuberculosis*, resting and IFN-γ activated murine macrophage cells were infected with either the wild type or mptpB mutant strain of *M. tuberculosis*. The number of surviving intracellular bacteria was determined on days 0, 2, 4, 6 and 8 post-infection. Both parental as well as the mptpB mutant strain displayed a similar pattern of intracellular growth at all time points of study (FIG. 8A). While at the initial time point (day 0) the bacillary counts were approximately $10^4$ cfu/well, the bacillary load increased at later time points attaining the peak values of $~10^5$ cfu at 8 days post-infection. These results showed that both parental as well as the mptpB mutant strain exhibited comparable capacity of infection and multiplication in resting mouse macrophages. However, the two strains showed differences in their ability to survive in the activated macrophages. The number of wild type *M. tuberculosis* and mptpB mutant was maximum and comparable at the initial time point ($~10^4$ cfu/well, at day 0). At later time points, a reduction in the number of bacilli was observed in both cases. While the wild type *M. tuberculosis* was reduced to 50% and 28.6% at days 4 and 6 post-infection, respectively, a much sharper decline was noted in the case of mptpB mutant which was reduced to 10% and 4% at days 4 and 6 post-infection, respectively (FIG. 8B). These observations indicated that disruption of mptpB gene had impaired the ability of *M. tuberculosis* to survive in IFN-γ activated macrophages. The details of in vitro studies in macrophages are shown in Example 16.

To determine whether the disruption of mptpB gene would have any effect on the survival of *M. tuberculosis* in vivo, guinea pigs in groups of eight animals were infected subcutaneously with $5 \times 10^5$ cfu of either parental, mutant or the complemented strain of *M. tuberculosis*. Animals were euthanized three weeks and six weeks post-infection. At both time points of euthanization, spleens were homogenized and viable bacilli were enumerated (represented as $\log_{10}$ cfu for each group).

It was observed that at 3 weeks post-infection, the mean total score of the animals infected with mutant strain was 26, which was comparable to the scores in case of animals infected with parental (28) and complemented strain (30, FIG. 9A). These results were commensurate with the splenic cfu obtained for various groups on euthanization of animals at 3 weeks post-infection. The bacterial load in the spleen of animals infected with the mutant strain was $\log_{10} 3.71$, which was comparable to the bacterial load in the spleens of animals infected with parental ($\log_{10} 3.73$) and complemented strain ($\log_{10} 3.68$, FIG. 10A). However, the total scores of the animals infected with mutant strain at the end of six weeks was significantly lower (12) than the total score of animals infected with parental (35, p<0.02) and complemented strain (33, p<0.02, FIG. 9B). The animals infected with mutant strain exhibited a significant reduction of bacillary load in spleen ($\log_{10} 3.07$) when compared to bacillary load in spleen of animals infected with parental ($\log_{10} 4.77$, p<0.002) and complemented strain ($\log_{10} 4.45$, p<0.003, FIG. 10B). Thus, an approximately 3-fold reduction in total score and a 50 to 70-fold reduction in the bacillary load in spleens was observed in animals infected with mptpB mutant strain in comparison to parental or complemented strains.

Sections of liver and lung from animals in various groups were subjected to histological analysis to determine morphology of the organs, the presence and extent of granuloma and the type and number of infiltrating cells. It was observed that at three weeks there were no significant histological differences in liver and lung of animals infected with either parental, or mutant or complemented strain. At 3 weeks post-infection animals from all 3 groups showed no difference in the extent or composition of granuloma. In case of liver, granuloma consisted mainly of epitheloid cells and lymphocytes, while the lung granuloma comprised mainly of lymphocytes macrophages and a few epitheloid cells (FIGS. 11A and 11B). At six weeks post-infection, in the case of animals infected with wild type and complemented strain, the liver sections showed multiple well-defined granuloma comprising of epitheloid cells and lymphocytes. However, the liver tissue from animals infected with the mptpB mutant strain exhibited a distinct qualitative difference with respect to the presence of epitheloid cells with only a few lymphocytes. In case of lung tissues, the animals infected with the wild type and complemented strain showed extensive granulomas comprising of lymphocytes and macrophages. In contrast, the lung tissue from animals infected with the mutant strain showed partly organized granuloma mainly of lymphocytes (FIGS. 12A and 12B). The details of guinea pig studies is shown in Example 17.

Statistical Analysis

Data are depicted as arithmetic mean±standard error mean. Data were analyzed for statistical significance using the Student's t test. Differences between the guinea pig groups were considered significant if p values were <0.05.

Brief Description of the Accompanying Table:

TABLE 1

| Sequence listing | |
|---|---|
| SEQ ID NO: 1 | Primer A |
| SEQ ID NO: 2 | Primer B |
| SEQ ID NO: 3 | Primer C |
| SEQ ID NO: 4 | Primer D |
| SEQ ID NO: 5 | Primer E |
| SEQ ID NO: 6 | Primer F |
| SEQ ID NO: 7 | Primer G |
| SEQ ID NO: 8 | Primer H |
| SEQ ID NO: 9 | Primer I |
| SEQ ID NO: 10 | Primer J |
| SEQ ID NO: 11 | mptpA gene |
| SEQ ID NO: 12 | mptpB gene |
| SEQ ID NO: 13 | mptpAL (with flanking sequences) |
| SEQ ID NO: 14 | mptpBL (with flanking region) |
| SEQ ID NO: 15 | Modified mptpA |
| SEQ ID NO: 16 | Modified mptpB |

EXAMPLES

The following methods are listed to illustrate the invention and should not be construed to limit the scope of the invention.

Examples

Example 1

Source of Reagents and Chemicals Used

Reagents, chemicals and enzymes including media for growing culture were purchased from standard sources.

Example 2

Culturing of Bacterial Strains (*E. coli* and *Mycobacteria*)

*E. coli* was grown in either Luria Bertani medium or in 2XYT medium supplemented with either of the antibiotics; ampicillin (50 µg/ml); kanamycin (25 µg/ml); gentamycin (50 µg/ml) or hygromycin (150 µg/ml). *M. tuberculosis* Erdman was grown in Middlebrook 7H9 medium supplemented with 0.5% glycerol, 0.2% Tween-80 and 1× ADC supplement. The cultures were grown with constant shaking at 200 rpm, 37° C. Solid media included LB Agar in case of *E. coli* and 7H10/7H11 media containing 0.5% glycerol, 1XOADC supplement and appropriate antibiotics in case of *M. tuberculosis*.

Example 3

Isolation of Genomic DNA from *Mycobacteria*

*Mycobacteria* was grown to an $A_{600nm}$ of 2-3 and glycine was added to the culture at a final concentration of 1%. 24 hours after addition of glycine, cells were harvested by centrifugation at 8,000 rpm for 10 minutes at room temperature. The pellet was resuspended in 500 µl of TEG solutions and 50 µl of lysozyme (20 µg/ml) was added. After overnight incubation at 37° C., lysis was carried out by the addition of 100 µl of 10% SDS and 50 µl of Proteinase K (10 mg/ml) followed by incubation at 55° C. for 40 minutes. To the cell lysate, 200 µl of NaCl and 160 µl of CTAB was added and the suspension was incubated at 65° C. for 10 minutes. The lysate was extracted twice with phenol (pre-equilibrated with Tris-Hcl, pH 8.0) and twice with chloroform. The DNA was precipitated by adding $1/10^{th}$ volume of 3M sodium acetate and two volumes of chilled ethanol. The DNA pellet was then washed with 70% ethanol and resuspended in 100 µl of autoclaved double distilled water.

Example 4

Polymerase Chain Reaction (PCR)

Amplification of genes by PCR was carried out as per manufacturer's recommendations. All PCR reactions were performed by using Taq/Pfu mix. The sequences of oligonucleotides used are shown in Table 1. A typical amplification reaction contained 10 ng of template DNA, 1× Taq polymerase buffer, 200 µM dNTPs, and 20 pmoles each of forward and reverse primers, 1.5 mM $MgCl_2$ and 1 U of Taq/Pfu mix (Taq and Pfu DNA polymerase were mixed in a ration of 9:1).

A typical amplification reaction comprised of;
1. Initial denaturation at 94° C. for 5 minutes.
2. 30 cycles of denaturation at 94° C. for 45 seconds, annealing at 55° C.-65° C. for 1 minute and extension at 72° C. for 1 minute.
3. Final extension at 72° C. for 10 minutes.

The PCR products were resolved on 1.2% agarose gel and purified by using Qiagen gel extraction kit, as described above.

Example 5

Transformation of *E. coli*

*E. coli* XL-1 Blue and *E. coli* HB101 strains were grown in LB medium and competent cells were prepared by using the $CaCl_2$ method (Sambrook et al., 1989). For preparation of high efficiency transformation cells, *E. coli* strains were grown to an $A_{600\ nm}$ of 0.4-0.6 at 30° C. and chilled at 4° C. for 2 hours. The cells were harvested by pelleting the culture at 6,000 rpm at 4° C. for 15 minutes. The cell pellet was resuspended in ice-cold trituration buffer ($1/20^{th}$ of the original culture volume) and diluted to the original culture volume by using prechilled trituration buffer. After incubating on ice for 45 minutes, cells were harvested by centrifugation at 6,000 rpm for 10 minutes at 4° C. The cell pellet was gently resuspended on ice-cold trituration buffer ($1/10^{th}$ of the original volume). Glycerol was added drop wise with gentle swirling to a final concentration of 15% (v/v) and competent cells were stored in aliquots of 1 ml each at −70° C., till further use.

Transformation was carried out by the method described by Mandel and Higa (Mandel and Higa, 1970). The ligations or supercoiled DNA were mixed with 200 µl of cells and incubated on ice for 30 minutes. Cells were then subjected to heat shock at 42° C. for 45 seconds, followed by incubation on ice for 2 minutes. After incubating on ice, 800 µl of LB medium was added to the cells and the sample was incubated at 37° C. for one hr with constant shaking at 200 rpm. The transformants were selected on LB agar plates supplemented with the appropriate antibiotic(s).

Example 6

Preparation of Plasmid DNA from *E. coli* Transformants This was Carried out as per Following Protocols Separately A) Mini-Preparation of Plasmid DNA
(i) By Alkaline Lysis—Method:

A single colony was inoculated in 3 ml of 2XYT medium containing appropriate antibiotic(s) and grown overnight at 37° C. with shaking at 200 rpm. The cells were harvested by centrifugation at 6,000 rpm for 2 minutes at 4° C. The cell pellet was resuspended in 200 µl of TEG solution containing lysozyme (to a final concentration of 20 µg/ml) and the suspension was incubated at room temperature for 10 minutes. After incubating for 10 minutes 400 µl of freshly prepared alkaline—SDS solution was added followed by mixing and gentle inversion. After incubating on ice for 5 minutes, 300 µl of 3M potassium acetate was added, mixed by inversion and further incubated on ice for 10 minutes. The cell lysate was subjected to centrifugation at 12,000 rpm for 15 minutes at 4° C., followed by phenol chloroform extraction, followed by chloroform extraction, precipitated by adding 540 µl of isopropanol (0.6v/v) and DNA followed by centrifugation at 12,000 rpm for 10 minutes at room temperature. The pellet was washed twice with chilled 70% ethanol, air-dried and resuspended in 50 µl of TE buffer.

(ii) By Boiling Lysis Method:

The bacterial culture was grown and harvested as described above. The cell pellet was resuspended in 600 µl of STET solution containing lysozyme (to a final concentration of 20 µg/ml). After incubating for 15 minutes at room temperature, the cell suspension was boiled at 100° C. for 2 minutes. The clarified cell lysate was prepared by subjecting the crude cell lysate to centrifugation at 12,000 rpm for 15 minutes at room temperature. The DNA was precipitated by adding 600 µl of ammonia mix solution and recovered by centrifugation at 12,000 rpm for 10 minutes at room temperature. The pellet was washed twice with chilled 70% ethanol, air-dried and resuspended in 50 µl of TE buffer.

(iii) By Qiagen Miniprep Kit:

The bacterial culture was grown and harvested as described above. The pellet was resuspended in 250 µl of buffer P1 and incubated at room temperature for 5 minutes. After incubating for 5 minutes, 250 µl of buffer P2 was added and mixed by gentle inversions. After incubating for 5 minutes, 350 µl of buffer N3 was added and incubated on ice for 5 minutes and the clarified cell lysate was prepared by centrifugation at 12,000 rpm at 4° C. for 15 minutes. The supernatant was passed through the Qia column, followed by washing with 500 µl of buffer PB. The column was then washed twice with 750 µl of buffer PE. The purified DNA was eluted in 100 µl of elution buffer.

Maxi Preparation of DNA:

Plasmid DNA was isolated on a large scale by the alkaline SDS method (Sambrook et al 1989). A single colony was inoculated in 200 ml of 2XYT medium containing appropriate antibiotic(s) and grown overnight at 37° C. with shaking at 200 rpm. The cells were harvested by centrifugation at 6,000 rpm for 15 minutes at 4° C. The cell pellet was resuspended in 4 ml of Solution I containing lysozyme (to a final concentration of 20 µg/ml). The sample was incubated on ice for 30 minutes. After incubating on ice for 30 minutes, 8 ml of freshly prepared Solution II was added and the sample was further incubated on ice for 15 minutes. Then, 6 ml of Solution III was added and incubated on ice for 10 minutes. The clarified cell lysate was prepared by centrifugation at 12,000 rpm for 15 minutes at 4° C. The DNA was precipitated from the cell lysate by addition of 10.8 ml of isopropanol (0.6v/v). After incubating at room temperature for 10 minutes, plasmid DNA was recovered by centrifugation at 12,000 rpm for 15 minutes at room temperature. The pellet was washed twice with chilled 70% ethanol, air-dried and resuspended in 750 µl of TE buffer. The DNA was incubated with RNAaseA (20 µg/ml) for 30 minutes at 37° C., followed by extraction with phenol chloroform. DNA in the aqueous phase was precipitated by addition of 2.5 volumes of chilled absolute ethanol and sodium acetate to a final concentration of 0.3M. The DNA was incubated at −70° C. for 15 minutes, and DNA was recovered by centrifugation at 12,000 rpm for 15 minutes at 4° C. The pellet was washed twice with 70% ethanol, air-dried and resuspended in 100 µl of TE buffer.

Example 7

DNA Manipulations for Cloning Purposes

Restriction Digestion of DNA:

The restriction enzyme digestions of DNA were carried out at the specified temperature, as per manufacturer's recommendations. The analytical digestion was carried out in a reaction volume of 20 µl and preparative digestions were carried out in a reaction volume of 100 µl.

Dephosphorylation of DNA Termini:

Removal of 5' phosphate groups from DNA fragments was carried out by using Calf intestinal phosphatase. The DNA was incubated with the enzyme (1U) in 1× buffer at 37° C. for 30 minutes followed by incubation at 56° C. for 30 minutes. The enzyme was inactivated by incubating the reaction mixture at 65° C. for 10 minutes followed by phenol chloroform extraction and DNA was ethanol precipitated and resuspended in 10 µl of autoclaved double distilled water.

End Filling of 5' Overhang of DNA Fragment:

DNA fragment with 5' overhang was end repaired by using Klenow fragment of DNA polymerase-I. The DNA (50 ng/µl) was incubated with the enzyme (1-2U per µg of DNA) in 1× buffer containing 200 µM of dNTPs and incubated at 25° C. for 15 minutes, followed by heat inactivation at 75° C. for 15 minutes.

Ligation of DNA Termini:

All the ligation reactions were carried out in a volume of 10 µl at 25° C. for 3-4 hours. Each reaction contained typically 100 ng of the digested vector DNA, insert DNA fragment at 1:3 and 1:5 (vector:insert) molar concentrations and 1× ligase buffer containing 1 mM ATP and 40U of T4 DNA ligase. The ligation mixtures were then used to transform competent cells of *E. coli* XL1-Blue and transformants were selected on appropriate LB agar supplemented with appropriate antibiotic(s).

Example 8

Agarose Gel Electrophoresis

Agarose gel electrophoresis was carried out essentially as described earlier (Sambrook et al., 1989). DNA fragments of size >500 bp were resolved on 0.8% agarose gel, while those in the range of 250-500 bp were resolved on 1.2% agarose gel. The gels were electrophoresed in 1× TAE buffer containing 0.5 µg/ml ethidium bromide.

Example 9

Elution of DNA from Agarose

DNA was eluted from agarose gel by using the Qiagen gel extraction kit. The gel was excised out and incubated with 3 gel volumes of QG buffer, at 55° C. till the agarose was melted. The samples were then passed through Qia column, column was washed twice with PE buffer and the DNA was eluted in 50 µl of elution buffer.

Example 10

Immunoblot Analysis

Protein samples were resolved on 10% SDS-PAGE and then transferred to Hybond C extra membrane overnight at 40 mA or at 180 mA for 2 hours by using the Bio-Rad mini Trans Blot Cell (Bio-Rad Laboratories, Hercules, Calif., USA). Transfer of the protein to the membrane was confirmed by staining with Ponceau S stain. The membrane was blocked in 2% milk for 2 hours at room temperature. The blot was than incubated with 1:10,000 dilution of the polyclonal sera for 2 hours at room temperature. To prevent non-specific binding of antibody, the dilutions were prepared in 2% milk-PBST. The blot was then washed thrice with PBST. After washing, the blot was incubated with peroxidase conjugated goat anti-rabbit Immunoglobulin-G at a dilution of 1:2500. After incubation for 1 hour, the blot was washed thrice with PBST and the immunoreactive bands were visualized by the addition of PBS containing 10 µl/ml of 30% $H_2O_2$ and 0.5 mg/ml 3,3' diaminobenzidine tetrahydrochloride.

Example 11

DNA Sequencing

The DNA samples for sequencing were prepared from 3 ml culture of the respective transformants using the Qiagen prep spin plasmid kit. The DNA samples were sequenced by using an ABI Prism 377 sequencer with rhodamine dye terminator chemistry.

The sequencing PCR reaction was set up in a PE-2400 thermocycler (Perkin Elmer—Cetus, Norwalk, Conn., USA) by using 500 ng double stranded DNA and 3.2 pmol vector specific oligonucleotides. After completion of the sequencing reactions, the extension products were precipitated with sodium acetate and ethanol to remove un-incorporated terminators. The samples were than loaded onto a 4% long ranger gel. The sample lanes were analysed on a DNA sequencing analysis 3.0 software (ABI-Prism, Perkin Elmer Applied Biosystems, Foster City, Calif., USA).

Example 12

Electroporation of M. tuberculosis

M. tuberculosis cultures were grown to $A_{600\,nm}$ of 0.8 with shaking at 200 rpm at 37° C. Before harvesting, the cells were chilled on ice for one hour. Cells were pelleted by centrifugation at 6,000 rpm at 4° C. for 10 minutes, washed twice with chilled glycerol (10%), resuspended in 1 ml of chilled glycerol (10%) and stored in aliquots of 100 µl each at −70° C., till further use.

For electroporation, approximately 2 µg of DNA was mixed with 20 µl of cells, kept on ice for 15 minutes and cells were subsequently pulsed at field strength of 16 kV/cm (400 V input, 330 µF capacitance, 8 kOhms resistance, 2.4 kV output using cuvette with 0.15 cm gap width). Cells were recovered in 1 ml of 7H9 medium at 37° C., 200 rpm for 24 hours. The transformants were selected on Middlebrook 7H10 agar plates supplemented with ADC and containing appropriate antibiotic(s). Plates were incubated for 14-21 days at 37° C.

Example 13

Alkali and U.V. Pretreatment of DNA

The targeting DNA was pretreated with alkali before its electroporation into the competent cells of M. tuberculosis as per the method described by Hinds et al 1999 (Hinds et al., 1999). The vector was denatured in 20 µl of 0.2M NaOH containing 0.2 mM EDTA for 30 minutes at 37° C. The denatured DNA was precipitated by addition of $1/10^{th}$ volume of 3M sodium acetate and 2.5 volumes of chilled absolute ethanol. The DNA was precipitated by incubating the samples at −70° C. for 15 minutes and recovered by centrifugation at 12,000 rpm for 15 minutes at 4° C. The pellet was washed twice with chilled 70% ethanol to remove salts, air dried and resuspended in 10 µl of double distilled water. For U.V. pretreatment, DNA was subjected to U.V. irradiation in an U.V. stratalinker 1800 (Amersham) at 100-mJ $cm^{-2}$ for 5 minutes. For alkali and U.V. pretreatment of DNA, the DNA was prepared by Qiagen column as described above.

Example 14

Southern Blot Hybridization

The genomic DNA was isolated from M. tuberculosis, and subjected to restriction digestion by appropriate restriction endonuclease. The digested fragments were resolved on a 1.2% agarose gel at low voltage (40V) overnight in 1× TAE gel running buffer. The DNA fragments were depurinated by soaking the gel in 0.1N HCl for 10 minutes followed by a wash with double distilled water. The DNA was then denatured by soaking the gel in denaturation buffer (1.5M NaCl, 0.5 M NaOH), The gel was then rinsed with double distilled water and neutralized in neutralization buffer (1M Tris pH 7.4, 1.5 M NaCl). The DNA was then transferred to Hybond N membrane by capillary transfer in 20×SSC overnight (Southern 1975). The membrane was air-dried and DNA was cross-linked to the Hybond N membrane by U.V. irradiation for 2 minutes at 700 mJ. The blot was prehybridized in a solution containing 50% deionised formamide, 5× SSC, 5× Denhardts solution, 50 mM Tris-Cl, pH7.5 and 200 µg/ml denatured salmon sperm DNA overnight at 42° C. The heat denatured probe was then added to the blots and hybridization was carried out at 42° C. for 14-16 hours. The blot was washed first in 2× SSC and 0.1% SDS at room temperature for 30 minutes and then in 0.2× SSC and 0.1% SDS at room temperature for 30 minutes and then in 0.2× SSC and 0.2% SDS at 65° C. for 30 minutes. The blot was then air dried, wrapped in saran wrap and subjected to autoradiography.

Example 15

Preparation of Nucleic Acid Probes

The DNA fragment to be labeled was PCR amplified by using gene specific primers. The amplicon was purified by using Qiagen gel extraction kit and end-labeled by using NEBlot kit in a 50 µl reaction. The labeling reaction comprised of 10 ng of template DNA, 1× klenow buffer (having random primers), 1 mM dGTP, 1 mM dCTP, 1 mM dTTP and 10uCi of $\alpha^{32}$P dATP, 1U of klenow fragment. The template DNA was denatured at 100° C. for 5 minutes and kept in ice for 2 minutes, dNTPs and enzyme were added and end labeling was carried out at 37° C. for 2 hours. Unincorporated dNTPs were removed by using Qiagen nucleotide removal kit and the labeled probe was added to the blot.

Example 16

In Vitro Infection of Mouse Macrophage Cell Line by *M. tuberculosis*

J774A.1 mouse macrophage cell line (resting or activated with rIFN-γ 50 Uml$^{-1}$ for 16 hours) was seeded in a six well plate at a density of 2×10$^5$ per well. Before infection, the cell lines were washed once with 1× Hanks Balanced Salt Solution (HBSS) and medium was replaced with Dulbeccos modified eagle's medium (DMEM) supplemented with 10% heat inactivated fetal calf serum (FCS). The bacterial strains were washed twice with DMEM and resuspended in DMEM supplemented with 5% FCS. The cells were infected with wild type or mutant strain at an MOI of 1:10 (macrophage: bacteria). The cells were incubated at 37° C. in a 5% $CO_2$ atmosphere. After 6 hours of infection, cells were washed twice with 1× HBSS and overlayed with 2 ml DMEM supplemented with FCS (10%), Antibiotic-antimycotic (1%) and amikacin (20 µg/ml). On days 0, 2, 4, 6 and 8, infected cells were lysed in 1 ml of 0.1% Triton X-100 for 15 minutes. The number of bacilli at different time points was determined by plating 10-fold serial dilutions in duplicates on MB 7H10 medium and incubating the plates at 37° C. for 3 weeks.

Example 17

Virulence Studies in Guinea Pigs

The effect of disruption of tyrosine phosphatases on the virulence of *M. tuberculosis* was evaluated in the guinea pig model of experimental tuberculosis. This work was carried at Tuberculosis Research centre, Chennai. Random-Bred guinea pigs of the Duncan-Hartley strain in the weight range of 200-400 g were obtained from National Center for Laboratory Animal Science (NCLAS), Hyderabad.

The guinea pigs were divided into groups of sixteen each. Each group comprised of 16 animals, 8 males and 8 females. The different groups of guinea pigs were challenged with one of the organisms mentioned below-subcutaneously and 8 animals (4 males and 4 females) were euthanised at 3 weeks and 6 weeks post-challenge.

| | |
|---|---|
| a) *M. tuberculosis* Erdman<br>b) mptpA mutant strain | High Dose (5 × 10$^7$) |
| c) *M. tuberculosis* Erdman<br>d) mptpB mutant strain<br>e) mptpB complemented strain | Low Dose (5 × 10$^5$) |

All the organisms were coded and animals were subcutaneously challenged with all the coded preparations separately by using a 1 ml tuberculin syringe with a 26 G needle.

After euthanasia the following investigations were carried out

1) Gross body weight of the animal.
2) Weight of infected organs—liver, spleen and lung.
3) Scores of the gross pathological damage to the organs (Post-mortem scores).
4) Viable count of the tubercle bacilli from spleen and lung (Bacterial enumeration).
5) Histopathological evaluation of liver and lung.

The gross body weight of the animals was measured at the time of beginning of the experiment, and at weekly intervals till euthanasia. Liver, lungs, spleens and lymph nodes were removed aseptically and the weight of the infected organs was measured. The bacterial load was enumerated in spleens and lungs. Portions of liver and lung tissues were fixed in 10% formalin for histopathological analysis of granuloma formation and cellular composition of granuloma.

Post-Mortem Scores:

The virulence was measured based on the rate of progression of the disease in guinea pig as described by Mitichison. (Mitichison, 1964). At the post-mortem examination of the animals, the total extent of tuberculosis disease was assessed as a score ranging from 0 to 100. The extent of visible lesions in the organs were scored as described in Table 5. Average score for each group was calculated.

Viable Count of the Tubercle Bacilli from the Spleen and Lung:

The spleen and portion of lung was removed into a sterile, weighed grinding tube. Organs were homogenised in 5 ml of double distilled water by using a teflon homogenizer. Ten fold serial dilutions ($10^{-1}$, $10^{-2}$, $10^{-3}$, $10^{-4}$) were prepared in distilled water and 10 µl of neat homogenate and various dilutions were inoculated in LJ slopes in duplicates. The LJ slopes were incubated at 37° C. and readings for cfu were taken after 4 weeks and 6 weeks. The number of cfu per organ and an average organ cfu for each group was calculated. The sensitivity of this detection method was 500 bacilli.

Histopathology of Liver and Lungs:

The liver and lungs of the animals were removed and stored in preweighed jars containing 10% formaldehyde. Two bits of tissue (2 cm×2 cm thickness) each from liver and lung were fixed in 10% formalin until further treatment. The organ bits were washed in 70% alcohol and 95% alcohol for 2 hours each followed by treatment with isopropanol for 2 hours. In order to ensure complete dehydration of the tissue, the isopropanol treatment was repeated twice. The bits were then incubated in xylene for 15-20 minutes and finally embedded in molten paraffin wax. The paraffin embedded tissue portions was divided into 5 µm fine sections by using a microtome (Reichert, Germany) and fixed onto glass slides. Deparaffinization of the cut sections was carried out prior to staining. The slides were first immersed twice in xylene for 5 minutes each followed by treatment with isopropanol twice for 3 minutes each. The slides were finally treated with 95% alcohol for complete removal of traces of wax.

The sections were stained with hematoxylin and eosin for the presence of granuloma. The sections were washed in water and stained with hematoxylin for 5 minutes. Excess stain from the slide was removed by washing with distilled water. The slides were then counterstained with eosin solution for 1 minutes, washed with water and air-dried. For viewing the slides under the microscope, the slides were mounted using DPS mount and covered with a coverslip. The proportion of the granuloma and extent and type of cellular infiltration in the sections were microscopically assessed as described earlier (Ridley, 1977 and Jayashankar and Ramanathan, 1999). The tissue sections were analysed for following parameters to determine the effect of disruption of tyrosine phosphatases on the virulence of *M. tuberculosis*; size of typical granuloma; amount of caseous necrosis; relative number of neutrophils; macrophages; giant cells; epitheloid cells and lymphocytes; degree to which lymphocytes were organized in the granuloma and extent to which granuloma were organized. At least four different sections for each tissue were analyzed.

Statistical Analysis:

Data are depicted as arithmetic mean±standard error mean. Data were analyzed for statistical significance using the Student's t test. Differences between the various groups of guinea pig were considered significant if p values were <0.05.

REFERENCES

1. Andersson, K., Carballeira, N., Magnusson, K. E., Persson, C., Stendahl, O., Wolf-Watz, H. and Fallman, M. (1996) YopH of *Yersinia pseudotuberculosis* interrupts early phosphotyrosine signalling associated with phagocytosis. *Mol. Microbiol* 20: 1057-1069.
2. Azad, A. K., Sirakova, T. D., Fernandes, N. D. and Kolattukudy, P. E. (1997) Gene knockout reveals a novel gene cluster for the synthesis of a class of cell wall lipids unique to pathogenic mycobacteria. *J Biol Chem* 272: 16741-16745.
3. Azad, A. K., Sirakova, T. D., Rogers, L. M. and Kolattukudy, P. E. (1996) Targeted replacement of the mycocerosic acid synthase gene in *Mycobacterium bovis* BCG produces a mutant that lacks mycosides. *Proc Natl Acad Sci* 93: 4787-4792.
4. Balasubramanian, V., Pavelka, M. S., Bardarov, S. S., Martin, J., Weisbrod, T. R., McAdam, R. A., Bloom, B. R. and Jacobs, W. R. Jr (1996) Allelic exchange in *Mycobacterium tuberculosis* with long linear recombination substrates. *J Bacteriol* 178: 272-279.
5. Bardarov, S., Kriakov, J., Carriere, C., Yu, S., Vasmonde, C., Adam, R. M., Bloom, B. R., Hatfull, G. F. and Jacobs, W. R. Jr. (1997) Conditionally replicating mycobacteriophages: a system for transposon delivery to *Mycobacterium tuberculosis*. *Proc Natl Acad Sci* 94: 10961-10966.
6. Barnes, P. F., Bloch, A. B, Davidson, P. T. and Snider, D. E. (1991). Tuberculosis in patients with human immunodeficiency virus infection. *N. Eng. J. Med.* 324: 1644-1650.
7. Baulard, A., Kremer, L. and Locht, C. (1996) Efficient homologous recombination in fast growing and slow growing mycobacteria. *J Bacteriol* 178: 3091-3098.
8. Black, D. S., and Bliska, J. B. (1997) Identification of p130$^{cas}$ as a substrate of *Yersinia* YopH (Yop51), a bacterial protein tyrosine phosphatase that translocates into mammalian cells and targets focal adhesions. *EMBO J* 16: 2730-2744.
9. Bliska, J. B. and Black, D. S. (1995). Inhibition of the Fc receptor-mediated oxidative burst in macrophages by the *Yersinia pseudotuberculosis* tyrosine phosphatase. *Infect Immun* 63: 681-685.
10. Bliska, J. B., Guan, K., Dixon, J. E. and Falkow, S. (1991) Tyrosine phosphatase hydrolysis of host proteins by an essential *Yersinia* virulence determinant. *Proc Natl Acad Sci* 88: 1187-1191.
11. Bloch, A. B., G. M. Cauthen, G. M. Onorato, K. G. Dansbury, G. D. Kelly, C. R. Driver and D. E. Snider (1994). Nation-wide survey of dug resistant tuberculosis in the United States. *J. Am. Med. Assn.* 271: 665-671.
12. Cole, S. T., Brosch, R., Parkhill, J., Garnier, T., Churcher, C., Harris, D., Gordon, S. V., Eiglmeier, K., Gas, S., Barry, C. E., Tekala, F., Badcock, K., Basham, D., Brown, D., Chillingworth, T., Connor, R., Davies, R., Devlin, K., Feltwell, T., Gentles, S., Hamlin, N., Holroyd, S., Hornsby, T., Jagels, K., Krogh, A., McLean, J., Moule, S., Murphy, L., Oliver, K., Osborne, J., Quail, M. A., Rajandream, M. A., Rogers, J., Rutter, S., Seeger, K., Skelton, J., Squares, R., Squares, S., Sulston, J. E., Taylor, K., Whitehead, S, and Barrell, B. G. (1998) Deciphering the biology of *Mycobacterium tuberculosis* from the complete genome sequence. *Nature* 393: 537-544.
13. Dye, C., Scheele, S., Dolin, P., Pathania, V., and Ravglione, R. C. 1999. Global burden of tuberculosis—estimated incidence, prevalence, and mortality by country. *J. Am. Med. Assn.* 282: 677-686.
14. Fallman, M., Andersson, K., Hakansson, S., Magnusson, K. E., Stendahl, O., and Wolf-Watz, H. (1995) *Yersinia pseudotuberculosis* inhibits Fc receptor mediated phagocytosis in J774 cells. *Infect Immun* 63: 3117-3124.
15. Fu, Y., and Galan, J. E. (1999) A *Salmonella* protein antagonizes Rac-1 and Cdc42 to mediate host-cell recovery after bacterial invasion. *Nature* 401: 293-297.
16. Guilhot, C., Gicquel, B. and Martin, C. (1992) Temperature sensitive mutants of the *Mycobacterium* plasmid pAL5000. *FEMS Microbiol Lett* 98: 181-186.
17. Hinds, J., Mahenthiralingam, E., Kempsell, K. E., Duncan, K., Stokes, R. W., Parish, T., and Stoker, N. G. (1999) Enhanced gene replacement in mycobacteria. *Microbiology* 145: 519-527.
18. Horsburgh, C. R. (1991). *Mycobacterium avium* complex infection in the acquired immunodeficiency syndrome *N. Eng. J. Med.* 324: 1332-1338.
19. Jayashankar, K. and Ramanathan, V. D. (1999) Biochemical and histochemical changes relating to fibrosis following infection with *Mycobacterium tuberculosis* in the guinea pig. *Indian J Med Res* 110: 91-97.
20. Kaniga, K., Uralil, J., Bliska, J. B., and Galan, J. E. (1996) A secreted tyrosine phosphatase with modular effector domains in bacterial pathogen *Salmonella typhimurium*. *Mol. Microbiol.* 21: 633-641.
21. Koul, A., Choidas, A., Treder, M., Tyagi, A. K., Drlica, K., Singh, Y., and Ullrich, A. (2000) Cloning and characterization of secretory tyrosine phosphatase of *Mycobacterium tuberculosis*. *J. Bacteriol* 182: 5425-5432.
22. Mandel, M. and Higa, A. (1970) Calcium dependent bacteriophage infection. *J Mol Biol* 53: 159-162.
23. Mitchison, D. A. (1964) The virulence of tubercle bacilli from patients with pulmonary tuberculosis in India and other countries. *Bull Int Union Against Tuberculosis* 35: 287.
24. Myers, R. S., and Stahl, F. W. (1994) Chi and RecBCD enzymes of *Escherichia Coli*. *Annu Rev Genet.* 28: 49-70.
25. Parish, T., Gordon, B. G., McAdam, R. A., Duncan, K., Mizrahi, V. and Stoker, N. G. (1999) Production of mutants in amino acid biosynthetic genes of *Mycobacterium tuberculosis* by homologous recombination. *Microbiology* 145: 3497-3503.
26. Pelicic, V., Jackson, M., Reyrat, J. M., Jacobs, W. R., Gicquel, B. and Guilhot, C. (1997) Efficient allelic exchange and transposon mutagenesis in *Mycobacterium tuberculosis*. *Proc Natl Acad Sci* 94: 10955-10960.
27. Persson, C., Carballeira, N., Wolf-Watz, H. and Fallman, M. (1997) The PTPase YopH inhibits uptake of *Yersinia*, Tyrosine phosphorylation of p130$^{cas}$ and FAK, and the associated accumulation of these proteins in peripheral focal adhesions. *EMBO J.* 16: 2307-2318.

28. Raynaud, C., Guilhot, C., Rauzier, Y., Bordat, Y., Pelicic, V., Manganelli, R., Smith, I., Gicquel, B. and Jackson, M. (2002) Phospholipases C are involved in the virulence of *Mycobacterium tuberculosis*. *Mol Microbiol* 45: 203-217.
29. Reyrat, J. M., Berthet, F. X. and Gicquel, B. (1995) The urease locus of *Mycobacterium tuberculosis* and its utilization for the demonstration of allelic exchange in *Mycobacterium bovis* bacillus Calmette-Guerin. *Proc Natl Acad Sci* 92: 8768-8772.
30. Riley, M. and Labedan, B. (1997) Protein evolution viewed through *Escherichia Coli* protein sequences: introduction of the notion of a structural segment of homology, the module. *J Mol Biol* 268: 857-868.
31. Ruckdeschel, K. A., Roggenkamp, A., Schubert, S. and Heesemann, J. (1996) Differential contribution of *Yersinia enterolitica* virulence factors to evasion of microbicidal action of neutrophils. *Infect Immun* 64: 724-733.
32. Sambandamurthy, V. K., Wang, X., Chen, B., Russell, R. G., Derrick, S., Collins, F. M., Morris, S. L. and Jacobs, W. R. (2002) A pantothenate auxotroph of *Mycobacterium tuberculosis* is highly attenuated and protects mice against tuberculosis. *Nature Medicine* 8: 1171-1174.
33. Sambrook, J., Fritsch, E. F. and Maniatis, T. (1989) Molecular cloning. In a laboratory manual. Cold Spring Harbour Laboratory Press, Cold Spring Harbour, N.Y.
34. Sauvonnet, N., Lambermont, I., Vari der Bruggen, P. and Cornelis, G. R. (2002) YopH inhibits monocyte chemoattractant protein 1 expression in macrophages and T-cell proliferation through inactivation of the phosphatidylinositol 3-kinase pathway. *Mol Microbiol* 45: 805-815.
35. Sory, M. P., Boland, A., Lambermont, I. and Cornelis, G. R. (1995) Identification of the YopE and YopH domains required for secretion and internalization into the cytosol of macrophages using the cyaA gene fusion approach. *Proc Natl Acad Sci* 92: 11998-12002.

We claim:

1. A mutant strain of *mycobacterium* comprising in its genome a modified tyrosine phosphatase gene mptpA comprising SEQ ID No. 15, the strain being incapable of expressing active tyrosine phosphatase.

2. The mutant strain of claim 1, wherein the *mycobacterium* is of a species selected from a group consisting of *M. tuberculosis* and *M. bovis*.

3. An isolated nucleic acid comprising SEQ. No. 15.

4. The mutant strain of claim 1, wherein the modified tyrosine phosphatase gene mptpA consists of SEQ ID NO:15.

5. A primer consisting of SEQ ID NO:1, SEQ ID NO:2, SEQ ID NO:3, or SEQ ID NO:4.

6. The isolated nucleic acid of claim 3, further comprising a nucleic acid encoding a second antibiotic resistance marker.

7. The isolated nucleic acid of claim 6, wherein the nucleic acid encoding the second antibiotic resistance marker imparts resistance to kanamycin or gentamycin.

* * * * *

SEQUENCE LISTING

```
<160> NUMBER OF SEQ ID NOS: 16

<210> SEQ ID NO 1
<211> LENGTH: 32
<212> TYPE: DNA
<213> ORGANISM: Artificial Sequence
<220> FEATURE:
<223> OTHER INFORMATION: Primer

<400> SEQUENCE: 1
ccatcatgac gtcgtctgac aacggagcgt cc                                     32

<210> SEQ ID NO 2
<211> LENGTH: 32
<212> TYPE: DNA
<213> ORGANISM: Artificial Sequence
<220> FEATURE:
<223> OTHER INFORMATION: Mycobacterium tuberculosis

<400> SEQUENCE: 2
gggcatatgg caacaccccg gccgcccgct cg                                     32

<210> SEQ ID NO 3
<211> LENGTH: 33
<212> TYPE: DNA
<213> ORGANISM: Artificial Sequence
<220> FEATURE:
<223> OTHER INFORMATION: Mycobacterium tuberculosis

<400> SEQUENCE: 3
gggcatatga cgctcggctg ttgcggcagc tcg                                    33

<210> SEQ ID NO 4
<211> LENGTH: 32
<212> TYPE: DNA
<213> ORGANISM: Artificial Sequence
<220> FEATURE:
<223> OTHER INFORMATION: Mycobacterium tuberculosis

<400> SEQUENCE: 4
ccatcatgac ggtggctggc cccgcggtgc gg                                     32

<210> SEQ ID NO 5
<211> LENGTH: 33
<212> TYPE: DNA
<213> ORGANISM: Artificial Sequence
<220> FEATURE:
```

```
<223> OTHER INFORMATION: Mycobacterium tuberculosis

<400> SEQUENCE: 5
ccatcatgac tgtggaacct attcctgtcg gcc                                 33

<210> SEQ ID NO 6
<211> LENGTH: 36
<212> TYPE: DNA
<213> ORGANISM: Artificial Sequence

```
gtgttgcgag cccacggcta ccctaccgac caccgggccg cacaagtcgg caccgaacac 240
ctggcggcag acctgttggt ggccttggac cgcaaccacg ctcggctgtt gcggcagctc 300
ggcgtcgaag ccgcccgggt acggatgctg cggtcattcg acccacgctc gggaacccat 360
gcgctcgatg tcgaggatcc ctactatggc gatcactccg acttcgagga ggtcttcgcc 420
gtcatcgaat ccgccctgcc cggcctgcac gactgggtcg acgaacgtct cgcgcggaac 480
ggaccgagtt ga 492

<210> SEQ ID NO 12
<211> LENGTH: 831
<212> TYPE: DNA
<213> ORGANISM: Mycobacterium tuberculosis
<400> SEQUENCE: 12
tcatccgagc agcaccccgc gcatccggtt gactgtggcc tggctgatac cggcgtcgcg 60
caggtagccg cccagcgatc cgtaggtctc gtcaatggtc tggcgtgcgg cggccaggta 120
ctccgcgcgg acacccagga ccccgtcgga cagccgggcc ttggtgaacg tcaccacctc 180
gggtgccagt tcggtgtcga aacgctgctg gatcatctcg gagatccggg cccgcagttg 240
tggcacggag tcgttgctgc gcaggtagtc ggcgacgatg acgtcgcggt ccaggccgac 300
cgcttcaagc accagcgcga ccacgaagcc ggtgcgatcc ttacccgcga agcagtgggt 360
gagcaccggg cgtccggcgg caagcagtgt gacgacacga tgtagcgcgc gctgtgctcc 420
attgcgcgtt gggaattggc gatactcgtc ggtcatgtag cgggtggccg cgtcatttat 480
cgactggctg gattcgccgg actcgccgtt ggacccgtca ttggttagca gcctcttgaa 540
tgcggtttcg tgcggcgctg agtcgtcggc gtcatcatcg gcgaggtcgg ggaacggcag 600
caggtggacg tcgatgccgt ccggaacccg tcctggaccg cggcgggcaa cctcccggga 660
cgaccgcagg tcggcaacgt cggtgatccc cagccggcgc agcgttgccc ggccggcgtc 720
gtcgaggcgg ctcagctcgc tggaccggaa cagccgcccc ggccgcaatg cggttgcggt 780
gtcggcgacg tcacgaaagt tccacgcgcc cggcagttca cggacagcca t 831

<210> SEQ ID NO 13
<211> LENGTH: 2531
<212> TYPE: DNA
<213> ORGANISM: Mycobacterium tuberculosis
<400> SEQUENCE: 13
cgtcgtctga caacggagcg tccaaatcgt cgggcacgcg gtacacgcca tggtcaatgc 60
ctaaccgccg agtctcatga ggatgcagcg gcacaagctt tgctaccggc tcgccgcggc 120
gggcaatctc aacctctgcc cgccgtagac gagccgcagc agctcggaca ggcgtgtctt 180
cgcctcgtga acgccgaccc gcttcgcagg cgcccagact ttcgcgtcga ccacctgctc 240
accaaacttc gcgatcatcg cctgatacca cagcgccaac gggtagcggt ttgtccaacc 300
gcttcgtcaa cgacaatggg atcgtgaccg acacgaccgc gagcgggacc aattgcccgc 360
ctcctccacg cgccgccgca cggcgcgcat cgtcgccggg tgaatcgccg cagctggtga 420
tcttcgatct ggacggcacg ctgaccgact cggcgcgcgg aatcgtatcc agcttccgac 480
acgcgctcaa ccacatcggt gccccagtac ccgaaggcga cctggccact cacatcgtcg 540
gcccgcccat gcatgagacg ctgcgcgcca tggggctcgg cgaatccgcc gaggaggcga 600
tcgtagccta ccgggccgac tacagcgccc gcggttgggc gatgaacagc ttgttcgacg 660
ggatcgggcc gctgctggcc gacctgcgca ccgccggtgt ccggctggcc gtcgccacct 720

| | |
|---|---:|
| ccaaggcaga gccgaccgca cggcgaatcc tgcgccactt cggaattgag cagcacttcg | 780 |
| aggtcatcgc gggcgcgagc accgatggct cgcgaggcag caaggtcgac gtgctggccc | 840 |
| acgcgctcgc gcagctgcgg ccgctacccg agcggttggt gatggtcggc gaccgcagcc | 900 |
| acgacgtcga cggggcggcc gcgcacggca tcgacacggt ggtggtcggc tggggctacg | 960 |
| ggcgcgccga ctttatcgac aagacctcca ccaccgtcgt gacgcatgcc gccacgattg | 1020 |
| acgagctgag ggaggcgcta ggtgtctgat ccgctgcacg tcacattcgt ttgtacgggc | 1080 |
| aacatctgcc ggtcgccaat ggccgagaag atgttcgccc aacagcttcg ccaccgtggc | 1140 |
| ctgggtgacg cggtgcgagt gaccagtgcg ggcaccggga actggcatgt aggcagttgc | 1200 |
| gccgacgagc gggcggccgg ggtgttgcga gcccacggct acgctcggct gttgcggcag | 1260 |
| ctcggcgtcg aagccgcccg ggtacggatg ctgcggtcat tcgacccacg ctcgggaacc | 1320 |
| catgcgctcg atgtcgagga tccctactat ggcgatcact ccgacttcga ggaggtcttc | 1380 |
| gccgtcatcg aatccgccct gcccggcctg cacgactggg tcgacgaacg tctcgcgcgg | 1440 |
| aacggaccga gttgatgccc cgcctagcgt tcctgctgcg gcccggctgg ctggcgttgg | 1500 |
| ccctggtcgt ggtcgcgttc acctaccgt gctttacggt gctcgcgccg tggcagctgg | 1560 |
| gcaagaatgc caaaacgtca cgagagaacc agcagatcag gtattccctc gacaccccgc | 1620 |
| cggttccgct gaaaacccctt ctaccacagc aggattcgtc ggcgccggac gcgcagtggc | 1680 |
| gccgggtgac ggcaaccgga cagtaccttc cggacgtgca ggtgctggcc cgactgcgcg | 1740 |
| tggtggaggg ggaccaggcg tttgaggtgt tggccccatt cgtggtcgac ggcggaccaa | 1800 |
| ccgtcctggt cgaccgtgga tacgtgcggc cccaggtggg ctcgcacgta ccaccgatcc | 1860 |
| cccgcctgcc ggtgcagacg gtgaccatca ccgcgcggct gcgtgactcc gaaccgagcg | 1920 |
| tggcgggcaa agacccattc gtcagagacg gcttccagca ggtgtattcg atcaataccg | 1980 |
| gacaggtcgc cgcgctgacc ggagtccagc tggctgggtc ctatctgcag ttgatcgaag | 2040 |
| accaacccgg cgggctcggc gtgctcggcg ttccgcatct agatcccggg ccgttcctgt | 2100 |
| cctatggcat ccaatggatc tcgttcggca ttctggcacc gatcggcttg ggctatttcg | 2160 |
| cctacgccga gatccgggcg cgccgccggg aaaaagcggg gtcgccacca ccggacaagc | 2220 |
| caatgacggt cgagcagaaa ctcgctgacc gctacggccg ccggcggtaa accaacatca | 2280 |
| cggccaatac cgcagccccc gcctggacca cccgcgacag caccacgcg cggcgcagat | 2340 |
| cggccaccttt gggcgaccgg ccgtcgccca aggtgggccg gatctgcaac tcatggtggt | 2400 |
| accgggtggg cccacccagc cgcacgtcaa gcgcccagc aaacgccgcc tcgacgacac | 2460 |
| cggcgttggg gctgggatgg cgggcggcgt cgcgccgcca ggcccgtacc gcaccgcggg | 2520 |
| gcgacccacc g | 2531 |

<210> SEQ ID NO 14
<211> LENGTH: 2890
<212> TYPE: DNA
<213> ORGANISM: Mycobacterium tuberculosis

<400> SEQUENCE: 14

| | |
|---|---:|
| gtcggtgacc cccgtatagc ccggcgacgt cggtaattta gtagcgccct cgacctgcgc | 60 |
| gggcgtgagg tccaaatact tggtgtgtac gaatgtgatg cctgcaaccg cgttgaggtc | 120 |
| ggaaatgaag ttgagcgggt atcgcgagaa gtcggcgaac ccgtcgtact cgagcgtgta | 180 |
| gatggccgtc ggatagatcg tgtccgaggg cgttgcgcca tagaacgtca ggtccagagt | 240 |
| cggaagcgtc agatccggga accgcgcgag cataccgcca ttggggttca tttcattgcc | 300 |

-continued

```
gacaagcacg aaattgaggt cgctcgccga aggtgcggcc ccgcccatcg ccgtgaacct    360
ctgcatctcc agcgacgcga ttatggcgct ttgcgaccag ccgaaaacgg tgaccgcgtt    420
tccggtggtc gcgagctcta ccatgatcgc gtcgtgcaag atggtcaagc cctcttccac    480
tgacgtgttg aggaccaaac ttctgacacc ggtgagtggg tacaactctt cgggtgtgaa    540
gacggcttgt agcgcccgcc gaacggacct acagcgtatt ggcggcgtca acatagacgg    600
cggtggtagt ggaattccgg tgggcccaaa gaacaaggtg gtcaagttcg ccgggaatgg    660
cggaatcatc gcggccgccg cggggggttgg tgcggcggcg ggcacagcca gctgattttg    720
ccgggtgctg gcgatggcgg cctcggcatc tgcgtagctg ttcgccgcgg cggccaacgt    780
ctggtggaac ctaactgtga aacgcctcga cttgagcgag cacggcctgg tattcctggc    840
cgtatgcgcc gaacggtttc gcgatggcgg ccgacacctc atcgccggcc gccgcggcca    900
gtgcacacgt cgggcctgcc gcggccgcgc cggccgtact cacggccgaa ccgattcctg    960
ccacctcggc ggcggccgcc gctacgatcc gcggctcagc gatcagatac gacatcgtct   1020
cactccccta gcaccaggtg tcggccaacc gggtcaaccc ggggttttgg tcagcccaga   1080
gcggtccccg tgcctggtg gtcgcttacg cgaatcggat tcgcgcgaaa gcgtttcccc    1140
tcatccgagc agcaccccgc gcatccggtt gactgtggcc tggctgatac cggcgtcgcg   1200
caggtagccg cccagcgatc cgtaggtctc gtcaatggtc tggcgtgcgg cggccaggta   1260
ctccgcgcgg acacccagga ccccgtcgga cagccgggcc ttggtgaacg tcaccacctc   1320
gggtgccagt tcggtgtcga aacgctgctg gatcatctcg gagatccggg cccgcagttg   1380
tggcacggag tcgttgctgc gcaggtagtc ggcgacgatg acgtcgcggt ccaggccgac   1440
cgcttcaagc accagcgcga ccacgaagcc ggtgcgatcc ttacccgcga agcagtgggg   1500
gctggattcg ccggactcgc cgttggaccc gtcattggtt agcagcctct tgaatgcggt   1560
ttcgtgcggc gctgagtcgt cggcgtcatc atcggcgagg tcggggaacg gcagcaggtg   1620
gacgtcgatg ccgtccggaa cccgtcctgg accgcggcgg gcaacctccc gggacgaccg   1680
caggtcggca acgtcggtga tccccagccg gcgcagcgtt gcccggccgg cgtcgtcgag   1740
gcggctcagc tcgctggacc ggaacagccg ccccggccgc aatgcggttg cggtgtcggc   1800
gacgtcacga aagttccacg cgcccggcag ttcacggaca gccatctcag gtgaccgccg   1860
cagcgaaggt ggacttctcc ctcgacagct cggcgcgggc gatggagcgc aggtgcacct   1920
cgtcgggacc gtcgaagatg cgcatggcgc ggtgccagcc gtacaaccgg ccagcggggg   1980
tgtcgtcgct gacgccggcg gccccgtgga cctggattgc gcggtcgatg acatcgcagg   2040
ccacccgcgg ggccaccgcc ttgatcatgg cgaccaggtg gcgcgcctct tgttgccat    2100
gttggtcgat tgtccacgcc gccttttcgc acagcagcct tgcctggtcg atttcgttgc   2160
gggactgagc aatcgcctgt tgcacgacgc cctgttcggc tagcggacgg ccgaacgcca   2220
cccgttgcg gacgcgattc accatgagtg ccaaggcgcg ttcggccgcg cccagcgcac    2280
gcatgcagtg gtggatacgg cccggcccca gccgggcctg ggctatggcg aatccgctgc   2340
cctcttcgcc gagcaggttg gtggccggga cccgacgtt gtggtagtcg atctcgcagt    2400
ggccgtgccg gtcctgccag ccgaacaccg gtgtggagcg aacgatcgtc acgccggggg   2460
tgtcgatcgg gacgaggacc atcgactgct gttggtgggc ggctgcgtcc gggttggtgc   2520
ggcccatcac gatgaggatc ttgcaccgcg ggtccgccgc tcccgacgtc caccacttac   2580
ggccgttgat gacgtagtcg gcaccgtccc gggagatggt ggtttcgatg ttgcgggcgt   2640
cgctgctggc caccgccggc tcggtcatcg agaaggcgct gcggatcttg ccgtcgagca   2700
```

-continued

| | |
|---|---|
| gcggccgcag ccattgcgcc cgttgctgct cggtgccgaa catgtgcagg atctccatgt | 2760 |
| tgccggtgtc cggtgcggcg cagttgagtg cctcggcgc gatttccatg ctccatccgg | 2820 |
| tcatttcggc cagcggcgcg tactccaggt tggtcaatcc cgactcggcc gacaggaata | 2880 |
| ggttccacag | 2890 |

<210> SEQ ID NO 15
<211> LENGTH: 4163
<212> TYPE: DNA
<213> ORGANISM: Artificial sequence
<220> FEATURE:
<223> OTHER INFORMATION: Mycobacterium tuberculosis

<400> SEQUENCE: 15

| | |
|---|---|
| cgtcgtctga caacggagcg tccaaatcgt cgggcacgcg gtacacgcca tggtcaatgc | 60 |
| ctaaccgccg agtctcatga ggatgcagcg gcacaagctt gctaccggc tcgccgcggc | 120 |
| gggcaatctc aacctctgcc cgccgtagac gagccgcagc agctcggaca ggcgtgtctt | 180 |
| cgcctcgtga acgccgaccc gcttcgcagg cgcccagact ttcgcgtcga ccacctgctc | 240 |
| accaaacttc gcgatcatcg cctgatacca cagcgccaac gggtagcggt ttgtccaacc | 300 |
| gcttcgtcaa cgacaatggg atcgtgaccg acacgaccgc gagcgggacc aattgcccgc | 360 |
| ctcctccacg cgccgccgca cggcgcgcat cgtcgccggg tgaatcgccg cagctggtga | 420 |
| tcttcgatct ggacggcacg ctgaccgact cggcgcgcgg aatcgtatcc agcttccgac | 480 |
| acgcgctcaa ccacatcggt gccccagtac ccgaaggcga cctggccact cacatcgtcg | 540 |
| gcccgcccat gcatgagacg ctgcgcgcca tggggctcgg cgaatccgcc gaggaggcga | 600 |
| tcgtagccta ccgggccgac tacagcgccc gcggttgggc gatgaacagc ttgttcgacg | 660 |
| ggatcgggcc gctgctggcc gacctgcgca ccgccggtgt ccggctggcc gtcgccacct | 720 |
| ccaaggcaga gccgaccgca cggcgaatcc tgcgccactt cggaattgag cagcacttcg | 780 |
| aggtcatcgc gggcgcgagc accgatggct cgcgaggcag caaggtcgac gtgctggccc | 840 |
| acgcgctcgc gcagctgcgg ccgctacccg agcggttggt gatggtcggc gaccgcagcc | 900 |
| acgacgtcga cggggcggcc gcgcacggca tcgacacggt ggtggtcggc tggggctacg | 960 |
| ggcgcgccga ctttatcgac aagacctcca ccaccgtcgt gacgcatgcc gccacgattg | 1020 |
| acgagctgag ggaggcgcta ggtgtctgat ccgctgcacg tcacattcgt ttgtacgggc | 1080 |
| aacatctgcc ggtcgccaat ggccgagaag atgttcgccc aacagcttcg ccaccgtggc | 1140 |
| ctgggtgacg cggtgcgagt gaccagtgcg ggcaccggga actggcatgt aggcagttgc | 1200 |
| gccgacgagc gggcggccgg ggtgttgcga gcccacggct tctagaggat ccccgggtac | 1260 |
| caagccctcg cgacgttcc gccgggcctc ggcgaccgcc cgtcgaggc gccggtcgga | 1320 |
| ggggcagtcc tccacgggca gctcgtggag ggcgcgggcc agctccgcca tcgcctcgac | 1380 |
| cacggcgaac cgctggtgct cgggccactc ctcggccgcc gcgacgccgg ggacggcctc | 1440 |
| cgtgacgagc cacgcggcgg tgtcgtcggc accgcgctcg acgacgcggg ggacggggat | 1500 |
| cggcggggcc tggcggcgcc tcgccgtcgc agaaccaggc ggtggcgtac accgtcgcct | 1560 |
| cggtcggccc gtagagattg gcgatcccga ccgcagcacc accgagaacg tccccgacgt | 1620 |
| ggccgaccag cccgtcatcg tcaacgcctg accgcggtgc ggacaggccg tgtcgcgacc | 1680 |
| ggccgtgcgg aattaagccg gccgtaccc tgtgaataga ggtccgctgt gacacaagaa | 1740 |
| tccctgttac ttctcgaccg tattgattcg gatgattcct acgcgagcct gcggaacgac | 1800 |
| caggaattct gggagccgct ggcccgccga gccctggagg agctcgggct gccggtgccg | 1860 |

```
ccggtgctgc gggtgcccgg cgagagcacc aaccccgtac tggtcggcga gcccgacccg    1920
gtcatcaagc tgttcggcga gcactggtgc ggtccggaga gcctcgcgtc ggagtcggag    1980
gcgtacgcgg tcctggcgga cgccccggtg ccggtgcccc gcctcctcgg ccgcggcgag    2040
ctgcggcccg gcaccggagc ctggccgtgg ccctacctgg tgatgagccg gatgaccggc    2100
accacctggc ggtccgcgat ggacggcacg accgaccgga acgcgctgct cgccctggcc    2160
cgcgaactcg gccgggtgct cggccggctg cacagggtgc cgctgaccgg aacaccgtg    2220 ctcaccccc attccgaggt cttccggaa ctgctgcggg aacgccgcgc ggcgaccgtc     2280
gaggaccacc gcgggtgggg ctacctctcg ccccggctgc tggaccgcct ggaggactgg    2340
ctgccggacg tggacacgct gctggccggc cgcgaacccc ggttcgtcca cggcgacctg    2400
cacgggacca acatcttcgt ggacctggcc gcgaccgagg tcaccgggat cgtcgacttc    2460
accgacgtct atgcgggaga ctcccgctac agcctggtgc aactgcatct caacgccttc    2520
cggggcgacc gcgagatcct ggccgcgctg ctcgacgggg cgcagtggaa gcggaccgag    2580
gacttcgccc gcgaactgct cgccttcacc ttcctgcacg acttcgaggt gttcgaggag    2640
accccgctgg atctctccgg cttcaccgat ccggaggaac tggcgcagtt cctctggggg    2700
ccgccggaca ccgcccccgg cgcctgacgc cccgggccgc ccggcgccgc cccggcccc     2760 cggcggccgc ccggagcccc gcccgcgctc gggagccccg ggcccgcgcc gaagcccgct    2820
gctgcgagcc cggagcgggc cggccgacgg cggtacccgg ggatcctcta gaacgctcgg    2880
ctgttgcggc agctcggcgt cgaagccgcc cgggtacgga tgctgcggtc attcgaccca    2940
cgctcgggaa cccatgcgct cgatgtcgag gatccctact atggcgatca ctccgacttc    3000
gaggaggtct tcgccgtcat cgaatccgcc ctgcccggcc tgcacgactg ggtcgacgaa    3060
cgtctcgcgc ggaacggacc gagttgatgc cccgcctagc gttcctgctg cggcccggct    3120
ggctggcgtt ggccctggtc gtggtcgcgt tcacctacct gtgctttacg gtgctcgcgc    3180
cgtggcagct gggcaagaat gccaaaacgt cacgagagaa ccagcagatc aggtattccc    3240
tcgacacccc gccggttccg ctgaaaaccc ttctaccaca gcaggattcg tcggcgccgg    3300
acgcgcagtg gcgccgggtg acggcaaccg gacagtacct tccggacgtg caggtgctgg    3360
cccgactgcg cgtggtggag ggggaccagg cgtttgaggt gttggcccca ttcgtggtcg    3420
acggcggacc aaccgtcctg gtcgaccgtg gatacgtgcg gccccaggtg ggctcgcacg    3480
taccaccgat ccccgcctg ccggtgcaga cggtgaccat caccgcgcgg ctgcgtgact     3540
ccgaaccgag cgtggcgggc aaagacccat tcgtcagaga cggcttccag caggtgtatt    3600
cgatcaatac cggacaggtc gccgcgctga ccggagtcca gctggctggg tcctatctgc    3660
agttgatcga agaccaaccc ggcgggctcg gcgtgctcgg cgttccgcat ctagatcccg    3720
ggccgttcct gtcctatggc atccaatgga tctcgttcgg cattctggca ccgatcggct    3780
tgggctattt cgcctacgcc gagatccggg cgcgccgccg ggaaaaagcg gggtcgccac    3840
caccggacaa gccaatgacg gtcgagcaga aactcgctga ccgctacggc cgccggcggt    3900
aaaccaacat cacggccaat accgcagccc ccgcctggac caccccgcgac agcaccacgg    3960 cgcggcgcag atcggccacc ttgggcgacc ggccgtcgcc caaggtgggc cggatctgca    4020
actcatggtg gtaccgggtg ggcccacccca gccgcacgtc aagcgccccca gcaaacgccg    4080 cctcgacgac accggcgttg gggctgggat ggcgggcggc gtcgcgccgc caggcccgta    4140
ccgcaccgcg gggcgaccca ccg                                           4163
```

<210> SEQ ID NO 16

-continued

<211> LENGTH: 4522
<212> TYPE: DNA
<213> ORGANISM: Artificial Sequence
<220> FEATURE:
<223> OTHER INFORMATION: Mycobacterium tuberculosis

<400> SEQUENCE: 16
gtcggtgacc cccgtatagc ccggcgacgt cggtaattta gtagcgccct cgacctgcgc 60
gggcgtgagg tccaaatact tggtgtgtac gaatgtgatg cctgcaaccg cgttgaggtc 120
ggaaatgaag ttgagcgggt atcgcgagaa gtcggcgaac ccgtcgtact cgagcgtgta 180
gatggccgtc ggatagatcg tgtccgaggg cgttgcgcca tagaacgtca ggtccagagt 240
cggaagcgtc agatccggga accgcgcgag cataccgcca ttggggttca tttcattgcc 300
gacaagcacg aaattgaggt cgctcgccga aggtgcggcc ccgcccatcg ccgtgaacct 360
ctgcatctcc agcgacgcga ttatggcgct ttgcgaccag ccgaaaacgg tgaccgcgtt 420
tccggtggtc gcgagctcta ccatgatcgc gtcgtgcaag atggtcaagc cctcttccac 480
tgacgtgttg aggaccaaac ttctgacacc ggtgagtggg tacaactctt cgggtgtgaa 540
gacggcttgt agcgcccgcc gaacggacct acagcgtatt ggcggcgtca acatagacgg 600
cggtggtagt ggaattccgg tggcccaaa gaacaaggtg gtcaagttcg ccgggaatgg 660
cggaatcatc gcggccgccg cgggggttgg tgcggcggcg ggcacagcca gctgattttg 720
ccgggtgctg gcgatggcgg cctcggcatc tgcgtagctg ttcgccgcgg cggccaacgt 780
ctggtggaac ctaactgtga aacgcctcga cttgagcgag cacggcctgg tattcctggc 840
cgtatgcgcc gaacggtttc gcgatggcgg ccgacacctc atcgccggcc gccgcggcca 900
gtgcacacgt cgggcctgcc gcggccgcgc cggccgtact cacggccgaa ccgattcctg 960
ccacctcggc ggcggccgcc gctacgatcc gcggctcagc gatcagatac gacatcgtct 1020
cactccccta gcaccaggtg tcggccaacc gggtcaaccc ggggttttgg tcagcccaga 1080
gcggtcccgc tgccctggtg gtcgcttacg cgaatcggat tcgcgcgaaa gcgtttcccc 1140
tcatccgagc agcaccccgc gcatccggtt gactgtggcc tggctgatac cggcgtcgcg 1200
caggtagccg cccagcgatc cgtaggtctc gtcaatggtc tggcgtgcgg cggccaggta 1260
ctccgcgcgg acacccagga ccccgtcgga cagccgggcc ttggtgaacg tcaccacctc 1320
gggtgccagt tcggtgtcga aacgctgctg gatcatctcg gagatccggg cccgcagttg 1380
tggcacggag tcgttgctgc gcaggtagtc ggcgacgatg acgtcgcggt ccaggccgac 1440
cgcttcaagc accagcgcga ccacgaagcc ggtgcgatcc ttacccgcga agcagtgggt 1500
ctagaggatc cccgggtacc aagccctcgg cgacgttccg ccgggcctcg gcgaccgccg 1560
cgtcgaggcg ccggtcggag gggcagtcct ccacgggcag ctcgtggagg gcgcgggcca 1620
gctccgccat cgcctcgacc acggcgaacc gctggtgctc gggccactcc tcggccgccg 1680
cgacgccggg gacggcctcc gtgacgagcc acgcggcggt gtcgtcggca ccgcgctcga 1740
cgacgcgggg gacggggatc ggcggggcct ggcggcgcct cgccgtcgca gaaccaggcg 1800
gtggcgtaca ccgtcgcctc ggtcggcccg tagagattgg cgatcccgac cgcagcacca 1860
ccgagaacgt ccccgacgtg gccgaccagc ccgtcatcgt caacgcctga ccgcggtgcg 1920
gacaggccgt gtcgcgaccg gccgtgcgga attaagccgg cccgtaccct gtgaatagag 1980
gtccgctgtg acacaagaat ccctgttact tctcgaccgt attgattcgg atgattccta 2040
cgcgagcctg cggaacgacc aggaattctg ggagccgctg gcccgccgag ccctggagga 2100
gctcgggctg ccggtgccgc cggtgctgcg ggtgcccggc gagagcacca accccgtact 2160

```
ggtcggcgag cccgacccgg tcatcaagct gttcggcgag cactggtgcg gtccggagag    2220
cctcgcgtcg gagtcggagg cgtacgcggt cctggcggac gccccggtgc cggtgccccg    2280
cctcctcggc cgcggcgagc tgcggcccgg caccggagcc tggccgtggc cctacctggt    2340
gatgagccgg atgaccggca ccacctggcg gtccgcgatg gacggcacga ccgaccggaa    2400
cgcgctgctc gccctggccc gcgaactcgg ccgggtgctc ggccggctgc acagggtgcc    2460
gctgaccggg aacaccgtgc tcaccccca ttccgaggtc ttcccggaac tgctgcggga    2520
acgccgcgcg gcgaccgtcg aggaccaccg cgggtggggc tacctctcgc cccggctgct    2580
ggaccgcctg gaggactggc tgccggacgt ggacacgctg ctggccggcc gcgaaccccg    2640
gttcgtccac ggcgacctgc acgggaccaa catcttcgtg gacctggccg cgaccgaggt    2700
caccgggatc gtcgacttca ccgacgtcta tgcgggagac tcccgctaca gcctggtgca    2760
actgcatctc aacgccttcc ggggcgaccg cgagatcctg gccgcgctgc tcgacggggc    2820
gcagtggaag cggaccgagg acttcgcccg cgaactgctc gccttcacct tcctgcacga    2880
cttcgaggtg ttcgaggaga ccccgctgga tctctccggc ttcaccgatc cggaggaact    2940
ggcgcagttc ctctggggc cgccggacac cgccccggc gcctgacgcc ccgggccgcc    3000
cggcgccgcc cccggccccc ggcggccgcc cggagcccg cccgcgctcg ggagcccgg    3060
gcccgcgccg aagcccgctg ctgcgagccc ggagcgggcc ggccgacggc ggtacccggg    3120
gatcctctag aggctggatt cgccggactc gccgttggac ccgtcattgg ttagcagcct    3180
cttgaatgcg gtttcgtgcg gcgctgagtc gtcggcgtca tcatcggcga ggtcggggaa    3240
cggcagcagg tggacgtcga tgccgtccgg aacccgtcct ggaccgcggc gggcaacctc    3300
ccgggacgac cgcaggtcgg caacgtcggt gatccccagc cggcgcagcg ttgcccggcc    3360
ggcgtcgtcg aggcggctca gctcgctgga ccggaacagc cgccccggcc gcaatgcggt    3420
tgcggtgtcg cgacgtcac gaaagttcca cgcgcccggc agttcaccga cagccatctc    3480
aggtgaccgc cgcagcgaag gtggacttct ccctcgacag ctcggcgcgg gcgatggagc    3540
gcaggtgcac ctcgtcggga ccgtcgaaga tgcgcatggc gcggtgccag ccgtacaacc    3600
gggccagcgg ggtgtcgtcg ctgacgccgg cggcccgtg acctggatt gcgcggtcga    3660
tgacatcgca ggccacccgc ggggccaccg ccttgatcat ggcgaccagg tggcgcgcct    3720
cttggttgcc atgttggtcg attgtccacg ccgccttttc gcacagcagc cttgcctggt    3780
cgatttcgtt gcgggactga gcaatcgcct gttgcacgac gccctgttcg gctagcggac    3840
ggccgaacgc cacccggttg cggacgcgat tcaccatgag tgccaaggcg cgttcggccg    3900
cgcccagcgc acgcatgcag tggtggatac ggcccggccc cagccgggcc tgggctatgg    3960
cgaatccgct gccctcttcg ccgagcaggt tggtggccgg gacccggacg ttgtggtagt    4020
cgatctcgca gtggccgtgc cggtcctgcc agccgaacac cggtgtggag cgaacgatcg    4080
tcacgccggg ggtgtcgatc gggacgagga ccatcgactg ctgttggtgg gcggctgcgt    4140
ccggggttggt gcggcccatc acgatgagga tcttgcaccg cgggtccgcc gctcccgacg    4200
tccaccactt acgccgttg atgacgtagt cggcaccgtc ccgggagatg gtggtttcga    4260
tgttgcgggc gtcgctgctg gccaccgccg gctcggtcat cgagaaggcg ctgcggatct    4320
tgccgtcgag cagcggccgc agccattgcg cccgttgctg ctcggtgccg aacatgtgca    4380
ggatctccat gttgccggtg tccggtgcgg cgcagttgag tgcctcgggc gcgatttcca    4440
tgctccatcc ggtcatttcg gccagcggcg cgtactccag gttggtcaat cccgactcgg    4500
ccgacaggaa taggttccac ag                                            4522
```